US012653698B2

(12) United States Patent
Freeman et al.

(10) Patent No.: US 12,653,698 B2
(45) Date of Patent: Jun. 16, 2026

(54) SYSTEMS AND METHODS FOR TREATING A SACROILIAC JOINT

(71) Applicant: University of South Florida, Tampa, FL (US)

(72) Inventors: Thomas B. Freeman, Tampa, FL (US); Thomas G. Hoghaug, Chanhassen, MN (US)

(73) Assignee: University of South Florida, Tampa, FL (US)

( * ) Notice: Subject to any disclaimer, the term of this patent is extended or adjusted under 35 U.S.C. 154(b) by 392 days.

(21) Appl. No.: 18/224,116

(22) Filed: Jul. 20, 2023

(65) Prior Publication Data

US 2023/0355408 A1     Nov. 9, 2023

Related U.S. Application Data

(63) Continuation of application No. PCT/US2022/013561, filed on Jan. 24, 2022.

(60) Provisional application No. 63/141,094, filed on Jan. 25, 2021.

(51) Int. Cl.
*A61F 2/46*       (2006.01)
*A61B 17/17*      (2006.01)
*A61F 2/30*       (2006.01)

(52) U.S. Cl.
CPC ........ *A61F 2/4603* (2013.01); *A61B 17/1739* (2013.01); *A61F 2/30749* (2013.01); *A61F 2002/30263* (2013.01); *A61F 2002/30266* (2013.01); *A61F 2002/30995* (2013.01)

(58) Field of Classification Search
CPC ................ A61F 2/4603; A61F 2/30749; A61F 2002/3063; A61F 2002/30266; A61F 2002/30995; A61B 17/1739
See application file for complete search history.

(56) References Cited

U.S. PATENT DOCUMENTS

| | | | |
|---|---|---|---|
| 7,648,509 B2 | 1/2010 | Stark | |
| 8,454,618 B2 | 6/2013 | Stark | |
| 8,778,026 B2 | 7/2014 | Mauldin | |
| 9,119,732 B2 * | 9/2015 | Schifano | ............ A61B 17/7055 |
| D742,517 S | 11/2015 | Schifano | |
| 9,333,090 B2 * | 5/2016 | Donner | .............. A61B 17/7055 |

(Continued)

OTHER PUBLICATIONS

International Search Report for PCT/US2022/013561 with a filing date of Jan. 24, 2022.

(Continued)

*Primary Examiner* — Kevin T Truong
*Assistant Examiner* — Diana Jones
(74) *Attorney, Agent, or Firm* — Molly L. Sauter; Anton J. Hopen; Trenam Law

(57) ABSTRACT

A method of treating a sacroiliac joint and/or a region proximate the sacroiliac joint includes distracting and/or stabilizing a recess between a sacral wall of a sacrum and an ilial wall of an ilium, cutting a surface of the ilial wall using a cutting device, and positioning an implant having a first planar wall and a second planar wall opposite the first planar wall into the recess, such that the first planar wall of the implant is in contact with an uncut surface of the sacral wall, and the second planar wall is in contact with the cut surface of the ilial wall. The implant can be formed as a wedge-shape, a double-wedge shape, or a cuboid shape.

10 Claims, 16 Drawing Sheets

(56)          References Cited

U.S. PATENT DOCUMENTS

|  |  |  |  |  |
|---|---|---|---|---|
| 9,421,109 | B2 | 8/2016 | Donner et al. | |
| 9,492,284 | B2 | 11/2016 | Ginn et al. | |
| 9,700,356 | B2 | 7/2017 | Donner et al. | |
| 9,788,961 | B2 | 10/2017 | Donner et al. | |
| 10,596,004 | B2 * | 3/2020 | Donner .............. | A61B 17/1626 |
| 2008/0021454 | A1 | 1/2008 | Chao et al. | |
| 2009/0024174 | A1 | 1/2009 | Stark | |
| 2009/0216238 | A1 | 8/2009 | Stark | |
| 2010/0106200 | A1 | 4/2010 | Stark | |
| 2010/0268228 | A1 | 10/2010 | Petersen | |
| 2013/0144343 | A1 | 6/2013 | Arnett et al. | |
| 2014/0277460 | A1 * | 9/2014 | Schifano ............ | A61B 17/8605 |
| | | | | 606/86 R |
| 2015/0173805 | A1 | 6/2015 | Donner et al. | |
| 2015/0250611 | A1 | 9/2015 | Schifano et al. | |
| 2016/0310197 | A1 | 10/2016 | Black et al. | |
| 2019/0343640 | A1 | 11/2019 | Donner et al. | |
| 2020/0000605 | A1 | 1/2020 | Shanks | |

OTHER PUBLICATIONS

International Preliminary Report on Patentability for PCT/US2022/013561 with a filing date of Jan. 24, 2022.
Supplementary European Search Report for Application No. EP22743341, dated Nov. 11, 2024.

\* cited by examiner

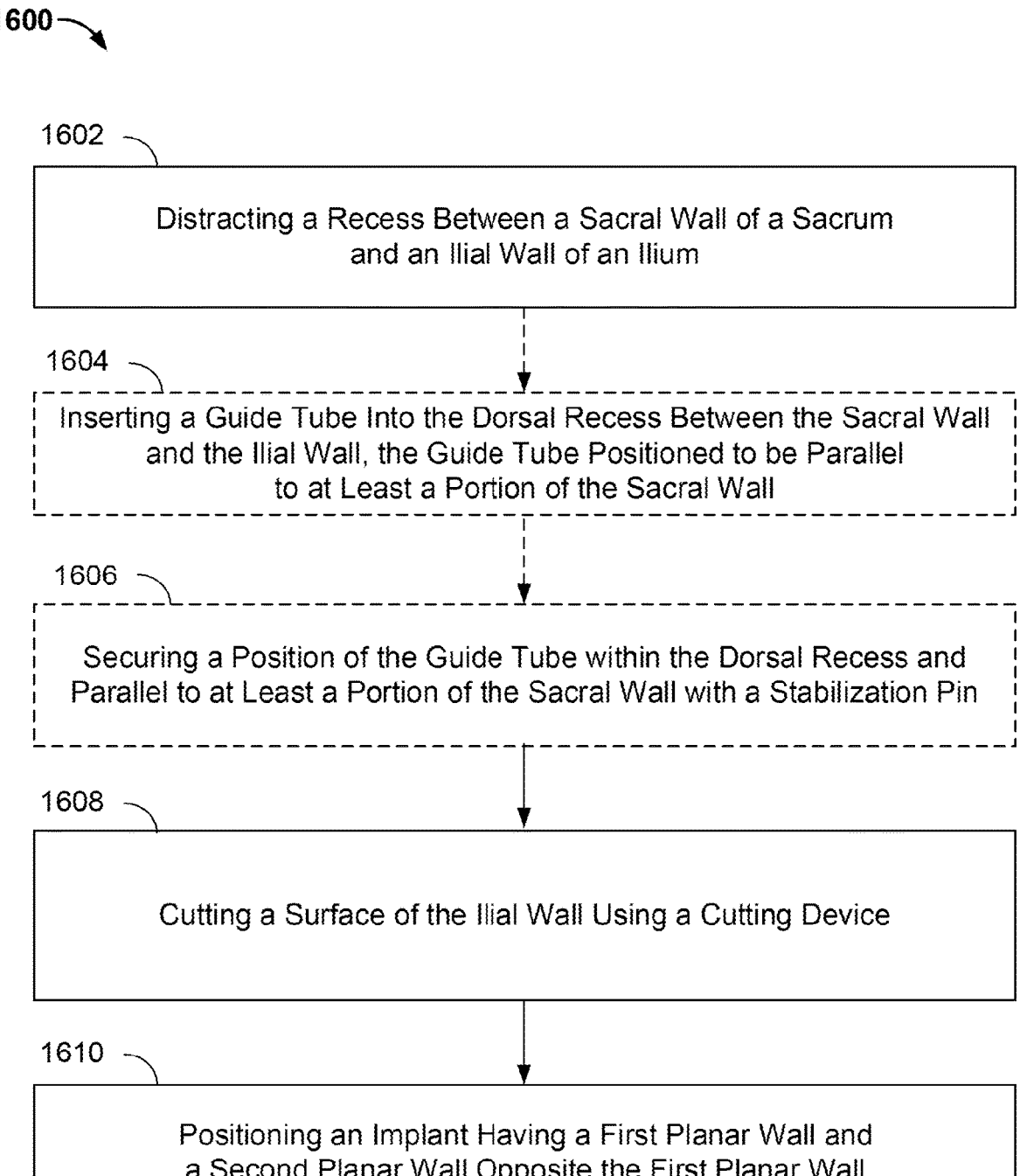

1602 ⟍

Distracting a Recess Between a Sacral Wall of a Sacrum
and an Ilial Wall of an Ilium

1604 ⟍

Inserting a Guide Tube Into the Dorsal Recess Between the Sacral Wall
and the Ilial Wall, the Guide Tube Positioned to be Parallel
to at Least a Portion of the Sacral Wall

1606 ⟍

Securing a Position of the Guide Tube within the Dorsal Recess and
Parallel to at Least a Portion of the Sacral Wall with a Stabilization Pin

1608 ⟍

Cutting a Surface of the Ilial Wall Using a Cutting Device

1610 ⟍

Positioning an Implant Having a First Planar Wall and
a Second Planar Wall Opposite the First Planar Wall
into the Distracted Recess such that the First Planar Wall
of the Implant is in Contact with an Uncut Surface of the Sacral Wall
and the Second Planar Wall is in Contact with
the Cut Surface of the Ilial Wall

FIG. 16

SYSTEMS AND METHODS FOR TREATING A SACROILIAC JOINT

CROSS-REFERENCE TO RELATED APPLICATIONS

This application is a continuation of and claims priority to International Application No. PCT/US22/13561, filed on Jan. 24, 2022, which claims the benefit of U.S. Provisional Application No. 63/141,094, filed Jan. 25, 2021, the disclosure of which is incorporated herein by reference in its entirety for all purposes.

TECHNICAL FIELD

This specification generally relates to technology for treating bones, for example, surgically stabilizing, and/or fusing bones.

BACKGROUND

Sacroiliac joint (SIJ) pain is a common affliction from which many patients suffer. The sacroiliac joint is located at or near the sacral bone (sacrum) and iliac bone (ilium) in the pelvic region. There are many defects, diseases, and conditions that cause SIJ pain, and reasons underlying the pain can be difficult to diagnose.

Conventional methods of treating SIJ pain involve surgical implantation of a cylindrical implant between the sacrum and ilium, extending into the cortex of the sacral bone and the cortex of the ilial bone. The sacrum, and the lateral sacrum (sacral ala) in particular, is a considered to be a "soft" bone and has low bone density. Ultimately, many implants used for fusing the sacrum and ilium cause subsidence of the implant into the sacral wall, resulting in failure of the implant and requiring additional surgeries.

Additionally, conventional devices are typically implanted via a lateral approach. The lateral approach to the SIJ requires navigating multiple muscle groups and avoiding damage to nerve roots in the SI joint and pelvis. Implantation by the lateral approach is complicated and can result in injury to surrounding tissue and vasculature. For example, injury to the superior gluteal artery laterally, or the iliac artery and vein in the pelvis, can also occur during implantation of a device by the lateral approach.

As a result, there is a need for safer and more effective treatments for SIJ pain.

SUMMARY

Surgical implantation of a device through a posterior approach can prevent many of the issues associated with lateral approach. The posterior approach provides a trajectory into the dorsal recess (i.e., a recess in a SIJ region that is formed between the sacrum and ilium) for distraction, and additionally or alternatively stabilization, of the SIJ and implantation of an implant device with less risk of injury to muscles, nerves, and veins in the region, including nerves over the top of sacrum, nerves in the sacral foramen, or intra-abdominal injuries of nerves, arteries, veins, and organs.

In various embodiments described herein, an implant has walls with a sufficiently large surface area for contacting the sacral and ilial walls that is less likely to cause subsidence of the implant into the sacral wall (a common cause of fusion failure and loss of device efficacy), and may additionally encourage bone fusion. In some embodiments, an implant with a wedged or double-wedged shape can approximate the double-wedge shape of the dorsal recess in a patient in order to optimize load sharing along a larger surface area of the implant. The larger surface area of the implant surface for load sharing abuts the sacral wall and can prevent subsidence of the implant into the sacrum, which can occur when implant surfaces having small surface area are adjacent to and push against the soft sacral wall. Subsidence of the implant into the sacral wall can occur when a round or elliptical implant is in contact with the bone at a thin line along the axis of the implant.

The implant also avoids disruption of the sacral cortex, another cause of implant subsidence into the soft sacral walls. Instead of removing portions of (e.g., violating) the sacral cortex to implant the device, a method of implantation can be utilized which includes cutting and/or removing a portion of the ilial wall to accommodate the implant. This can eliminate the need to remove any material or at least reduce the need to violate the sacral cortex, or removal any of the lateral sacrum during implantation. The implant device can then be positioned so that a planar surface is facing the cut portion of the ilial wall, and an opposite planar surface can be positioned parallel to a surface of the intact sacral cortex. Because patient anatomy of the dorsal recess is highly variable, in some cases, multiple sizes of implants would need to be manufactured and available for implant depending on the particular size and shape of the recess. By cutting into the ilial wall and removing material from the ilium to accommodate the implant, the implant can be positioned in the recess of many patients despite differences in anatomy. Additionally, cutting into the harder iliac bone rather than sacral bone preserves the sacral cortex, minimizing the likelihood of subsidence of the implant into the sacrum.

To position the implant within the recess, a guide tube can optionally be used during the implantation procedure to ascertain that the implant is positioned with its planar walls generally aligned with (e.g., parallel to) the sacrum and ilium walls. More particularly, the sacral side of the implant is positioned with its planar wall generally aligned with and parallel to the lateral sacral wall. The guide tube can have one or more flat outer surfaces that can be aligned with the sacrum to ensure that the guide tube channel is generally parallel to the sacral wall. The guide tube can also include asymmetrical tangs extending from the distal end. The tangs can be sized to aid in positioning the guide tube in the dorsal recess, with one tang to be positioned in the recess at a particular spinal location (e.g., the S2 level) having a shape which is more steeply angled, narrower, or thinner than the other tang to be positioned at a different spinal location (e.g., the S1 level). The guide tube can advantageously help to align a cutting device (e.g., reamer) with the ilial wall to enable cutting into the sacral wall in the shape of the implant. The implant can then be positioned through the guide tube such that a planar wall of the implant is generally tangential to the sacrum, and not embedded into the sacrum or the sacral cortex. The implant can also optionally have fusion compatible surfaces on the load sharing sides of the implant such that bone grows or is encouraged to grow through, into, and/or onto the surface of the implant. The implant can also optionally have various surface features to prevent back-out or migration of the implant, and, alternatively or additionally, to prevent movement of the implant about the axis of nutation. The implant can also optionally include internal fixation mechanisms such as screw guides for fixing screws. In some embodiments, the internal fixation mechanism of the implant can help to prevent device pullout or migration of the device, or nutation of the sacroiliac joint. In some embodiments, the implant can serve as a secondary fixation device for other implanted devices in the body, such as a lumbo-sacral construct.

Because the method of implantation can include cutting into the ilial wall to accommodate the implant, this allows for only one or at least a smaller number of implant sizes and shapes to fit the recess anatomies of a wide range of patients. In some embodiments, a surgical implant kit could include two or three differently sized or shaped implants, a guide tube, and any other implements typically used for the surgical implantation, such as one or more distractors, rasps, curettes, box- or L-shaped cutters, reamers, hammers, stabilization pins, or combinations thereof.

In an aspect, a method of treating a sacroiliac joint and/or a region proximate the sacroiliac joint includes distracting a recess between a sacral wall of a sacrum and an ilial wall of an ilium, cutting a surface of the ilial wall using a cutting device, and positioning an implant having a first planar wall and a second planar wall opposite the first planar wall into the distracted recess, such that the first planar wall of the implant is in contact with an uncut surface of the sacral wall, and the second planar wall is in contact with the cut surface of the ilial wall.

In some implementations, each of the first and second planar walls of the implant are defined by at least one first side edge and a second side edge, the first side edge of the first planar wall is distanced from the first side edge of the second planar wall by a first separation distance, and the second side edge of the first planar wall is distanced from the second side edge of the second planar wall by a second separation distance, and the first separation distance is smaller than the second separation distance. In some implementations, the implant also includes third and fourth planar walls each extending between the first and second planar walls, the third planar wall extending between a third side edge of the first planar wall and a third side edge of the second planar wall, the fourth planar wall extending between a fourth side edge of the first planar wall and a fourth side edge of the second planar wall, and the third planar wall has a length shorter than that of the fourth planar wall.

In some implementations, the method also includes inserting a guide tube into the recess between the sacral wall and the ilial wall, positioning the guide tube within the recess using two distal tangs of the guide tube, the two distal tangs being asymmetrically formed to fit within the recess, anchoring, using a pin, the guide tube within the recess and parallel to at least a portion of the sacral wall, and inserting the implant into the recess through the guide tube. In some implementations, the method also includes creating a surgical access point for inserting the guide tube into the recess by a posterior approach. In some implementations, the implant is shaped as of one of a cuboid, a rectangular cuboid, a wedge-shaped cuboid, and a double-wedge-shaped cuboid.

In some implementations, the step of cutting a surface of the ilial wall using a cutting device includes inserting the cutting device through the guide tube, penetrating, with the cutting device, a portion of the ilium, and removing, with the cutting device, a portion of the ilial wall to form a cavity within the ilium. The sacral wall is not penetrated by the cutting device.

In some implementations, the method also includes inserting a screw through a hole of the implant into the ilial wall, the screw configured to serve as a base of a lumbo-sacral construct. In some implementations, the method also includes inserting at least one screw through a screw hole of the implant into at least one of the ilial wall and the sacral wall.

In another aspect, an implant for treating a sacroiliac joint and/or a region proximate the sacroiliac joint includes a first planar wall and a second planar wall opposite the first planar wall, and each of the first and second planar walls are defined by at least a first side edge and a second side edge. The first side edge of the first planar wall is distanced from the first side edge of the second planar wall by a first separation distance, and the second side edge of the first planar wall is distanced from the second side edge of the second planar wall by a second separation distance. The first separation distance is smaller than the second separation distance and the implant is a double-wedged cuboid.

In some implementations, the first and second sidewalls of the implant extend between the first and second planar walls, the second sidewall is opposite the first sidewall, and the second sidewall is a curved sidewall. In some implementations, at least one of the first and second planar walls includes a plurality of surface features having anchors perpendicular to the at least one of the first and second planar walls. In some implementations, the implant defines a cavity that extends from the first planar wall to the second planar wall, and the cavity is designed to receive a bone fusion material.

In another aspect, a guide tube for inserting an implant into a recess of a patient between an ilial wall and a sacral wall includes a first end, a second end opposite the first end, a wall extending from the first end to the second end, and first and second tangs. The wall forms a channel between the first end and the second end, and has a first flat surface and a second flat surface formed on an outer surface of the wall, each extending from the first end to the second end, and the first and second flat surfaces positioned opposite one another. The first and second tangs extend from the second end of the guide tube and are formed as flat extensions of the wall, each having a first edge extending distally from and parallel to the first flat surface of the wall, a distal tip, and a second tapered edge from the distal tip to the second flat surface of the wall.

In some implementations, the first flat surface of the guide tube is shaped and sized to be positioned in contact with a sacral wall in the recess of the patient. In some implementations, the first tang and the second tang are asymmetrical, and at least one of the length of the first edge, a width of the distal tip, or a shape of the second edge of the first tang are different than the second tang.

In another aspect, a kit for treating a sacroiliac joint and/or a region proximate the sacroiliac joint using an implant includes a plurality of implants, each implant having a double-wedge-shaped cuboid shape, and at least one guide tube. The guide tube includes a first end, a second end opposite the first end, a wall extending from the first end to the second end, and first and second tangs extending from the second end. The wall of the guide tube forms a channel between the first end and the second end. The guide tube has first and second flat surfaces formed on an outer surface of the wall extending from the first end to the second end, and the first and second flat surfaces are positioned opposite one another. The first and second tangs are formed as flat extensions of the wall, each having a first edge extending distally from and parallel to the first flat surface of the wall, a distal tip, and a second tapered edge from the distal tip to the second flat surface of the wall.

In some implementations, the kit also includes at least one of a rectangular-shaped cutting device, an L-shaped cutting device, a box-cutter, a box chisel, a curette, a distractor, a rasp, an inserting device, a removing device, a screw, a hammer, and a pin.

The details of one or more implementations are set forth in the accompanying drawings and the description below. Other features and advantages will be apparent from the description and drawings, and from the claims.

BRIEF DESCRIPTION OF THE DRAWINGS

FIG. 6A shows a perspective view of an exemplary implant device positioned between the sacral and ilial walls;

FIG. 6B shows another perspective view of an exemplary implant device positioned between the sacral and ilial walls;

FIG. 16 shows a flow chart of a method for stabilizing and fusing a sacroiliac joint or dorsal recess behind the sacroiliac joint.

DETAILED DESCRIPTION

Described below are various implementations of systems and method for treating a sacroiliac joint and/or a region proximate the sacroiliac joint. Various orthopedic implantable devices (referred to as "implants" or "devices" herein) that can be used in the treatment of SIJ pain, defect, disease, or degradation are described below. The implants can function to distract the dorsal recess or sacroiliac joint, and additionally or alternatively can stabilize the region by providing enough force to prevent the implant from migrating. Also described below are implementations or systems and methods for stabilizing a long lumbosacral construct with implants, with or without SIJ pathology. The implants can include planar surfaces to provide large surface area in contact with the sacral wall, and in some cases the ilial wall, when the implant is placed in a recess formed by the sacrum and ilium. In this document, the "dorsal recess" is defined to be a recess proximate the SIJ, which is bounded by the sacral wall and ilial wall. The implants described herein can be implanted in the dorsal recess, in a defect in a region of the SIJ, in a recess proximate the SIJ, or in another suitable recess formed between bones of the body. While the implants described below are described in the context of medical implants for human patients, the implants can also be used to treat various animals. Other aspects of the implants, implant systems, implant kits, and methods of surgically introducing the implants in patient anatomy will be discussed with reference to the figures, description below, and claims.

Figure 1A:
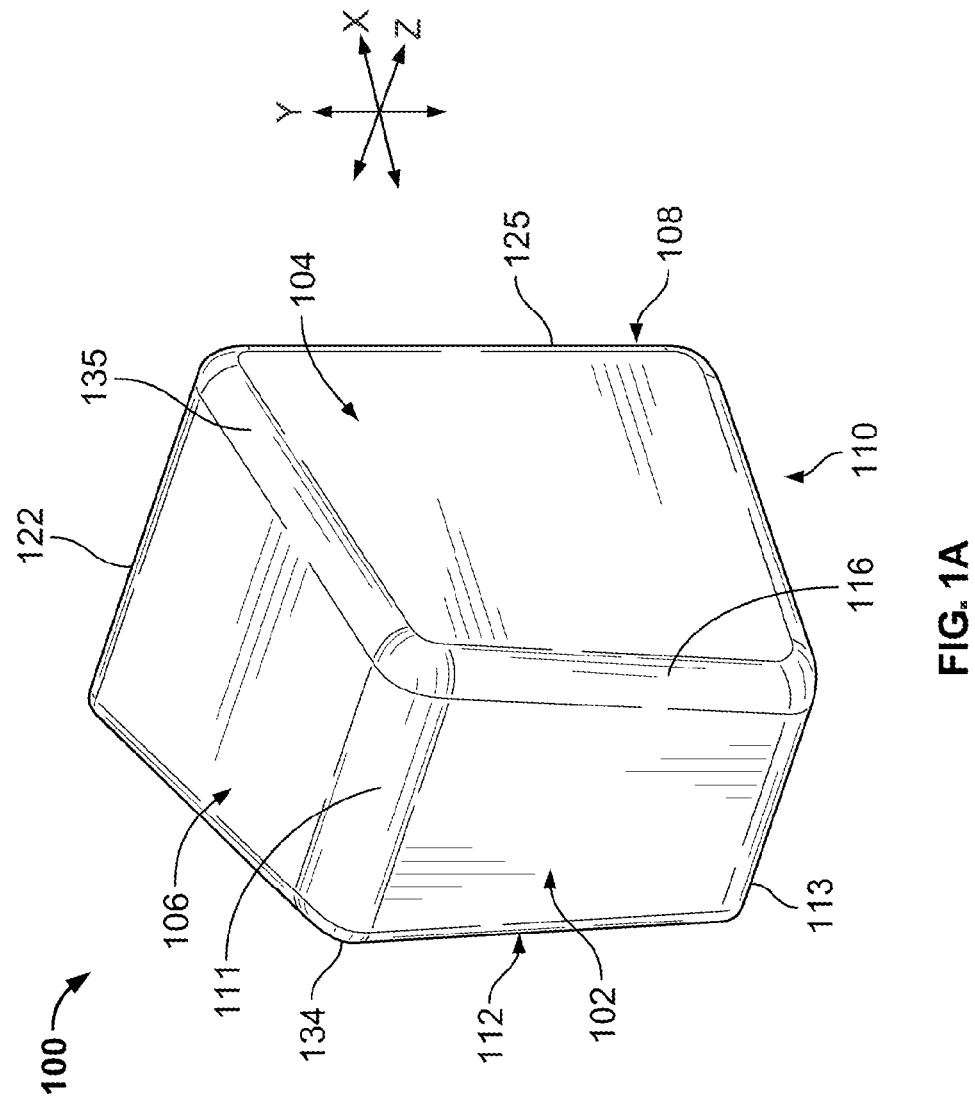
FIG. 1A shows a perspective view of an exemplary implant device.

FIG. 1A shows a perspective view of an exemplary implant device 100.

Figures 1B, 1C, 1D:
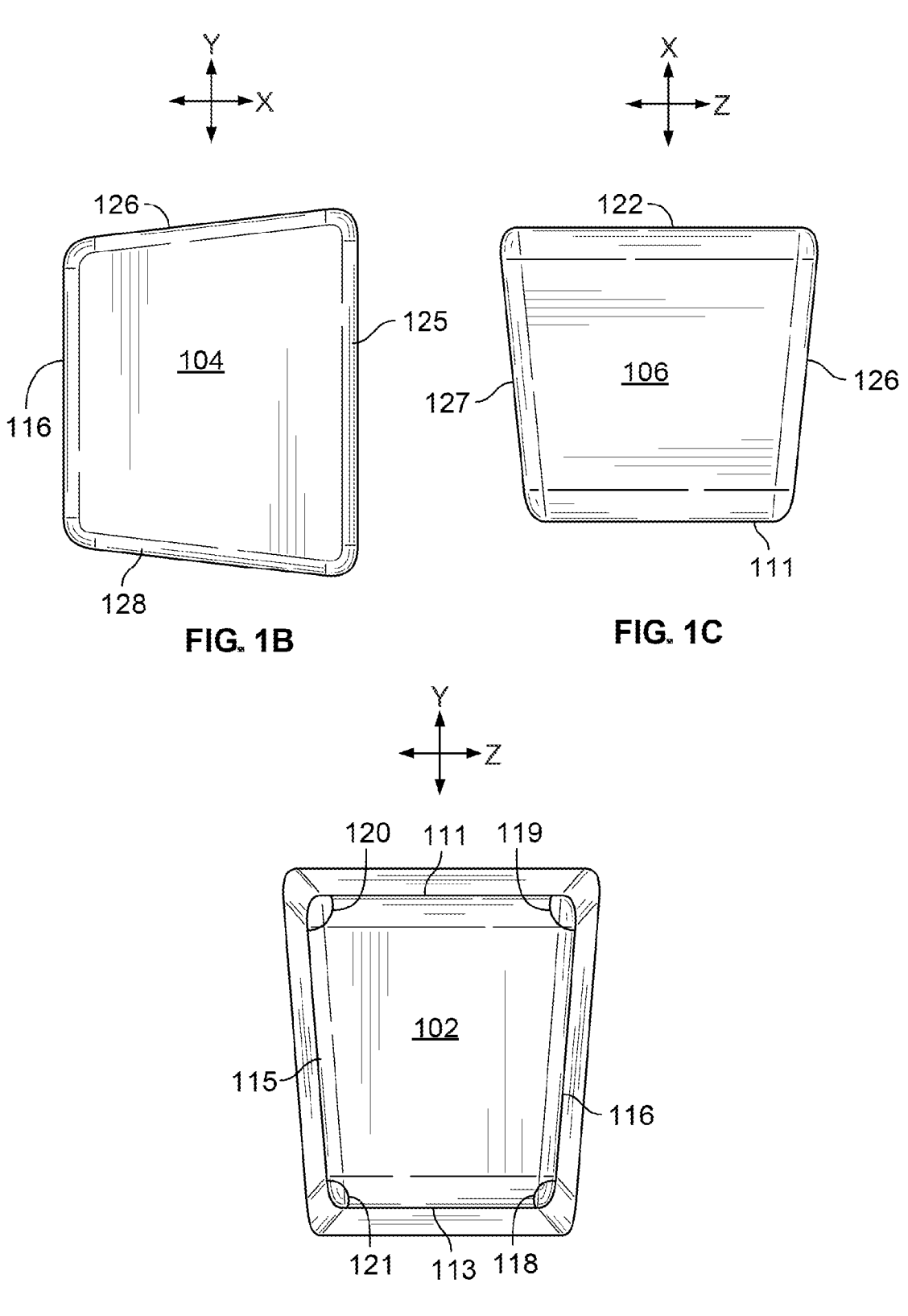
FIG. 1B shows a right side view of the implant device of FIG. 1A.
FIG. 1C shows a top view of the implant device of FIG. 1A.
FIG. 1D shows a front view of the implant device of FIG. 1A.
Figures 1E, 1F, 1G:
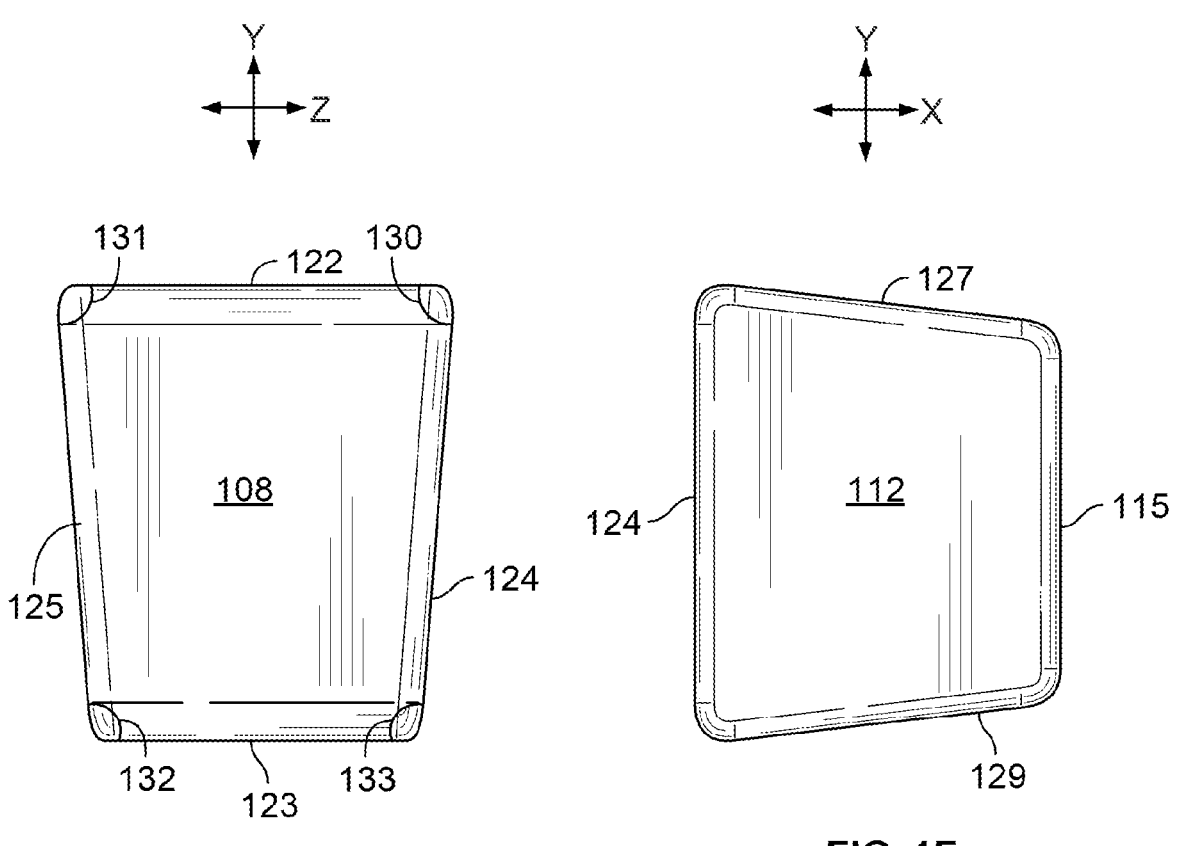
FIG. 1E shows a rear view of the implant device of FIG. 1A.
FIG. 1F shows a left side view of the implant device of FIG. 1A.
FIG. 1G shows a bottom view of the implant device of FIG. 1A.

FIGS. 1B-1G show various additional views of the implant device 100 of FIG. 1A. In particular, FIG. 1B shows a right side view of the implant, FIG. 1C shows a top view of the implant, FIG. 1D shows a front view of the implant, FIG. 1E shows a rear view of the implant, FIG. 1F shows a left side view of the implant, and FIG. 1G shows a bottom view of the implant.

FIG. 1A shows implant 100 having a leading edge surface 102, trailing edge surface 108, first planar side surface 104, second planar side surface 112 formed opposite the first planar side surface 104, anterior surface 106, and posterior surface 110. The six surfaces of the implant 100 each have four surrounding edges. The leading edge surface 102 (shown in front view FIG. 1D) includes first edge 111, second edge 116, third edge 113, and fourth edge 115. The trailing edge surface 108 (shown in back view FIG. 1E) includes fifth edge 122, sixth edge 124, seventh edge 123, and eighth edge 125. The leading edge surface 102 shares first edge 111 with anterior surface 106 (shown in top view FIG. 1C) and shares third edge 113 with posterior surface 110 (shown in bottom view FIG. 1G). The leading edge surface 102 also shares second edge 116 with right planar side surface 104 (shown in right side view FIG. 1B), and shares fourth edge 115 with left planar side surface 112 (shown in left side view FIG. 1F). The trailing edge surface 108 shares fifth edge 122 with anterior surface 106, shares sixth edge 124 with left planar side surface 112, shares seventh edge 123 with posterior surface 110, and shares eighth edge 125 with right planar side surface 104. Anterior surface 106 abuts right planar side surface 104 at ninth edge 126 and abuts left planar side surface 112 at tenth edge 127.

Posterior surface 110 abuts right planar side surface 104 at eleventh edge 128 and abuts left planar side surface 112 at twelfth edge 129.

The leading edge surface 102 is formed with a length of first edge 111 longer than a length of third edge 113, such that the second edge 116 and fourth edge 115 are angled relative to the Y-axis. Each of the corners of the leading edge surface 102 where the edges come together has an angle at which the edges meet. The leading edge surface 102 includes first angle 119 at the intersection of first edge 111 and second edge 116, second angle 118 at the intersection of second edge 116 and third edge 113, third angle 121 at the intersection of third edge 113 and fourth edge 115, and fourth angle 120 at the intersection of fourth edge 120 and first edge 111. Paired angles are formed between first angle 119 and fourth angle 120, and between second angle 118 and third angle 121. As shown, the paired angles can be angled relative to the y-axis such that the angles are equal but in opposite directions about the y-axis. In some implementations, the paired angles can have different angles relative to the y-axis. In some implementations, one angle of the paired angles has a 0 degree angle relative to the y-axis, i.e., the edge is parallel to the y-axis.

Like the leading edge, each of the corners of the trailing edge surface 108 where the edges come together has an angle at which the edges meet. The trailing edge surface 108 includes first angle 130, second angle 133, third angle 132, and fourth angle 131. Like the leading edge 102, the paired angles can be angled relative to the y-axis such that the angles are equal but in opposite directions about the y-axis. In some implementations, the paired angles can have different angles relative to the y-axis. In some implementations, one angle of the paired angles has a 0 degree angle relative to the y-axis, i.e., the edge is parallel to the y-axis. The angles of the trailing edge surface 108 can be equal to the angles of the leading edge surface 102 in some implementations.

A side edge of the leading edge surface 102 can be separated from a corresponding side edge of the trailing edge surface 108 by a smaller distance than a second side edge of the leading edge surface is separated from the corresponding side edge of the trailing edge surface. Each of the surfaces of the leading edge surface 102, trailing edge surface 108, first planar side surface 104, second planar side surface 112, anterior surface 106, and posterior surface 110 can be formed such that the surface is angled relative to a plane formed by the opposite surface of the implant 100. For example, in some implementations, the anterior surface 106 is smaller in a particular direction than the posterior surface 110 in the same direction.

The angled edges of the leading edge surface 102 and trailing edge surface 108 give the implant 100 a wedged shape, with the first edge 111 shared with the anterior surface 106 (and the fifth edge 122 shared with the anterior surface 106) being greater in length than the second edge 113 shared with the posterior surface 110 (and seventh edge 123 shared with the posterior surface 110) so that the leading edge surface 102 and trailing edge surface 108 are wider at a first side than at the opposite side. Additionally, because the first edge 122 of the trailing edge surface 108 is greater in length than the first edge 111 of the leading edge surface 102 (and the seventh edge 123 of the trailing edge surface 108 is greater in length than the third edge 113 of the leading edge surface 102), the implant 100 is also wedge-shaped from the leading edge surface 102 to the trailing edge surface 108. Each of the surfaces of the first planar side surface 104, second planar side surface 112, anterior surface 106, and posterior surface 110 are wedge shaped accordingly. The implant 100 has a double-wedged shape.

Each corner (for example, corner 134) of the implant 100 where three surfaces come together can be rounded, beveled, chamfered, or right-edged. Each edge (for example, edge 135) of the implant 100 can be rounded, beveled, chamfered, or right-edged.

Although the implant 100 is shown as a double-wedged shaped implant, in some implementations the implant 100 can have a different shape. In some implementations, the implant 100 can have a cuboid shape, a rectangular cuboid shape, a wedge-shaped cuboid, and a double wedge-shaped cuboid, and includes right angles, a favored angles, or symmetric angles.

Figures 2A, 2B, 2C:
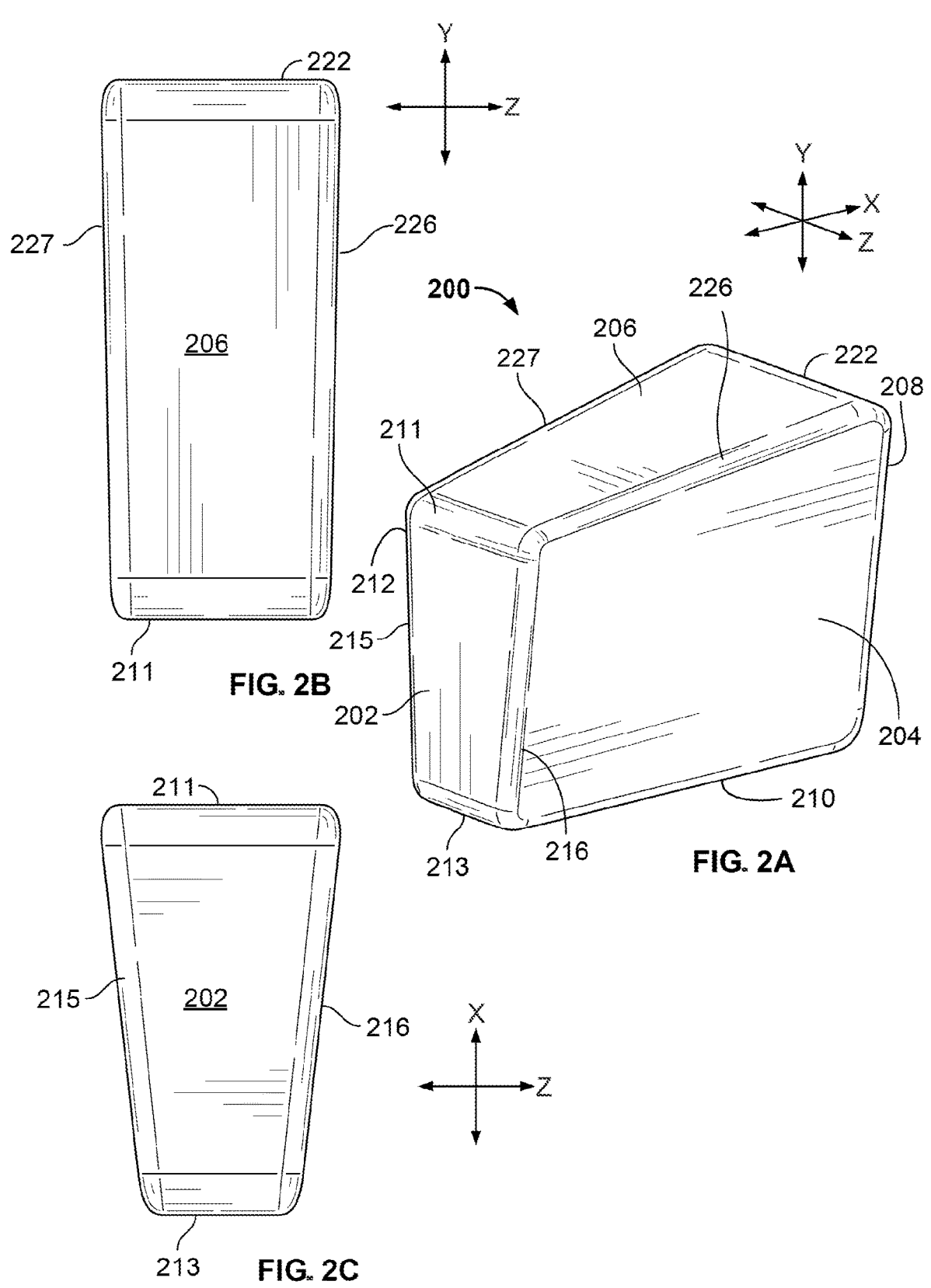
FIG. 2A shows a perspective view of an exemplary implant device.
FIG. 2B shows a top view of the implant device of FIG. 2A.
FIG. 2C shows a front view of the front planar surface of the implant device of FIG. 2A.

The double-wedged shape of the implant of FIG. 1A can be formed with different dimensions to be able to fit in the dorsal recess of patients with wider or narrower dorsal recesses. For example, the implant device illustrated in FIGS. 2A-C2 has a narrower double-wedged shape. FIG. 2A shows a perspective view of implant device for use in a patient with a narrower dorsal recess. FIG. 2B shows a front view of the implant device of FIG. 2A, and FIG. 2C shows a top view of the implant.

The implant 200 includes a leading edge surface 202, trailing edge surface 208, first planar side surface 204, second planar side surface 212 formed opposite the first planar side surface 204, anterior surface 206, and posterior surface 210. The six surfaces of the implant 200 each have four surrounding edges. The leading edge surface 202 (shown in FIG. 2C) includes first edge 211, second edge 216, third edge 213, and fourth edge 215. The anterior surface 206, sharing first edge 211 with the leading edge surface 202, also has four surrounding edges, including fifth edge 211 shared with leading edge surface 202, sixth edge 227, seventh edge 222, and eighth edge 226. Like the implant 100 in FIG. 1A-1G, the implant 200 is formed as a double-wedged shape. The implant 200 differs from the implant 100 in dimensions and angles of the edges with relation to each other. For example, the first and second planar side surfaces 212 and 204 are much longer in the direction from the leading edge surface 202 to the trailing edge surface 208. The third edge 213 is shorter than the corresponding edge of implant 100. These alterations in dimension can allow the implant to be used in patients who have differing anatomies of the dorsal region.

The implant can be manufactured in a variety of shapes and sizes to accommodate anatomical differences in patient dorsal recesses. The implant can be a double-wedged shape as illustrated in FIGS. 1A and 2A, with each planar side surface equally angled from a center axis passing through a center of the leading edge implant surface to the opposite implant surface (the back surface in FIGS. 1A and 2A, but the top surface when viewed from the posterior direction in the direction the implant is inserted into the dorsal recess). In some implementations, the planar side surfaces are not symmetrically angled from the center axis. One planar side surface may be formed at a greater angle from the center axis, forming a "favored angle." In each case, the two angles formed by the planar side surfaces relative to the center axis can sum to a total angle of 10 degrees, 12 degrees, 14 degrees, 15 degrees, 17 degrees, 18 degrees, 20 degrees, or any other suitable angle. For example, in a symmetrically angled configuration, each of the planar side surfaces can be angled 7 degrees from the center axis, such that the total angle is 14 degrees. In a non-symmetrically angled configuration, a first planar surface can be 10 degrees from the center axis, and the second planar surface can be angled 4 degrees from the center axis, for example. In a right-angled configuration, the first planar surface can be parallel to the center axis with no angle (0 degree angle), and the second planar surface is angled 14 degrees from the center axis. In some implementations, the implant can have a single-wedged shape. In some implementations, the first planar surface is parallel to the second planar surface, rather than angled.

Figure 3:
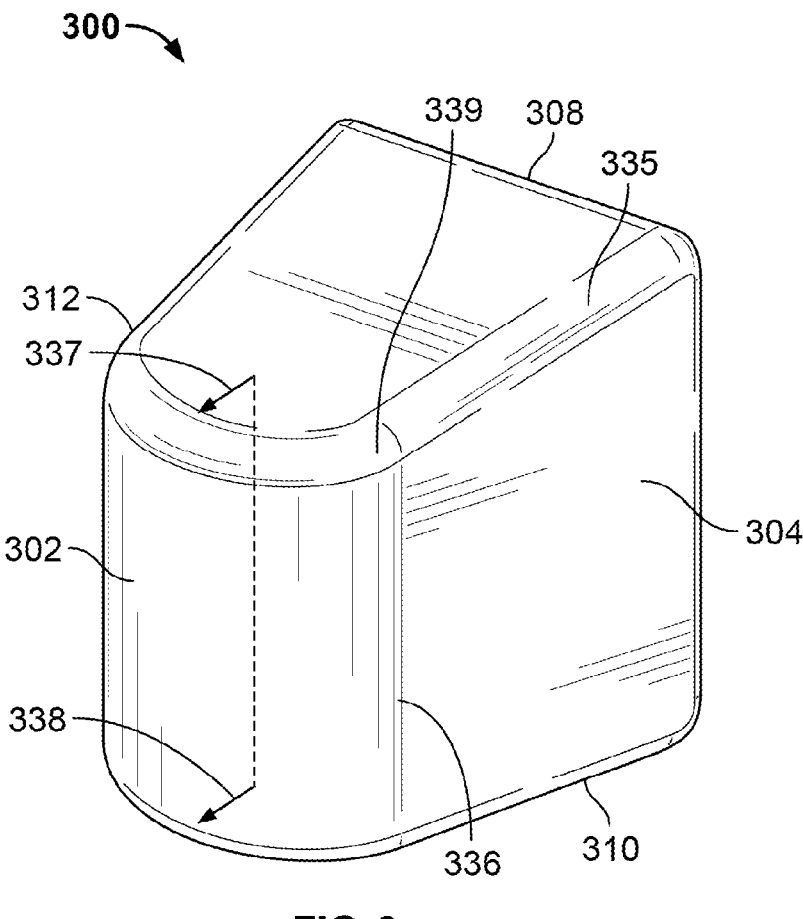
FIG. 3 shows a perspective view of an exemplary implant device.

While the implants of FIGS. 1A and 2A have flat leading edge implant surfaces, in some implementations, the leading edge implant surface can be rounded or bulleted. FIG. 3 shows a perspective view of an implant 300 having a rounded leading edge surface 302.

Implant 300 includes leading edge surface 302 formed as a rounded surface 339, trailing edge surface 308, first planar side surface 304, second planar side surface 312 formed opposite the first planar side surface 304, anterior surface 306, and posterior surface 310. Implant 300 also includes edge 335, intersection 336, first radius 337 and second radius 338.

The rounded surface 339 of the leading edge surface 302 is rounded from the first planar side surface 304 to the second planar side surface 312. The rounded surface 339 can smoothly transition into the first planar side surface 304 to the second planar side surface 312, or can have an intersection 336 formed as an angle with the first planar side surface 304, and to the second planar side surface 312 (not shown).

The anterior surface 305 and posterior surface 310 are bullet-shaped as a result of the rounded surface 339 of the leading edge surface 302. The rounded portion of the anterior surface 306 has a first radius 337 describing the curve of the edge between the anterior surface 306 and the leading edge surface 302. The rounded portion of the posterior surface 310 has a second radius 338 describing the curve of the edge between the posterior surface 310 and the leading edge surface 302. The first radius 337 may be smaller than the second radius 338, consistent with a wedge-shaped leading edge surface 302.

The first planar side surface 304 and the second planar side surface 312 are designed to abut the sacrum, and in some cases a portion of the ilial wall, when the implant is positioned in the dorsal recess. While the implant 300 is illustrated with a rounded surface 339 of the leading edge surface 302, in some implementations the rounded surface 339 is bulleted, so that it is rounded not only from the first planar side surface 304 to the second planar side surface 312, but also from the anterior surface 306 to the posterior surface 310 side. The rounded or bulleted the leading edge surface 302 helps to enable the positioning of the implant within the dorsal recess without catching on anatomical structures. If the implant impacts anatomical structures during insertion it could be rotated from its position as a result, and might impact the soft sacral wall. Rounded or bulleted leading edge implant surfaces can prevent this from occurring, as can chamfered, angled or rounded edges around the leading edge implant surface, as described above. Although the leading edge surface 302 is shown as having a rounded surface 339, in some implementations other surfaces of the implant 300 can be curved, rounded, shouldered, or irregular.

The wedged or double-wedged shape illustrated in FIGS. 1A-G, 2A-C, and 3 approximates (or "mimics") the wedge shape of most dorsal recesses. The dorsal recess is wedge-shaped in the dorsal/ventral direction, being wider at the dorsal or posterior portion of the recess and narrowing to the ventral or anterior portion. The dorsal recess is also wedge-shaped from in the rostral/caudal direction, being wider at the S1 level at the top of the iliac spine and narrowing toward the S2 level. The double-wedged shape can approximate both wedges of the dorsal recess, though as described above, other configurations and geometries of implant can also be used. For example, an implant can have cuboid shape, a rectangular cuboid shape, a wedge-shaped cuboid, and a double wedge-shaped cuboid, or any other suitable shape. Double-wedged shape implants, or implants of another shape, can be accommodated in the dorsal recess by cutting into the ilial wall in some implementations.

Figures 4A, 4B:
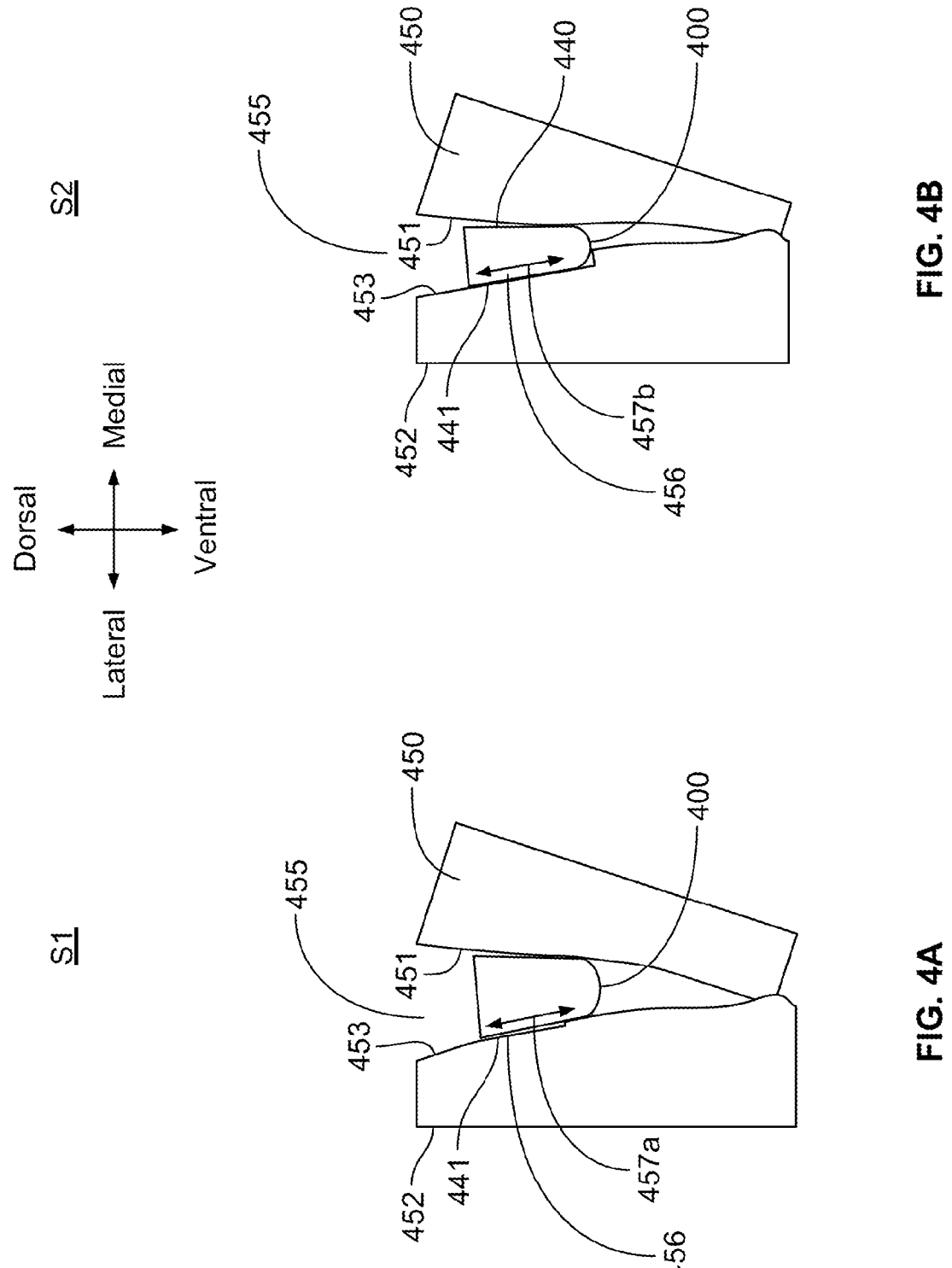
FIG. 4A shows an exemplary implant device positioned within a dorsal recess at the S1 level.
FIG. 4B shows an exemplary implant device positioned within a dorsal recess at the S2 level.

FIG. 4A shows a cross-section of an implant 400 positioned within a dorsal recess 455 at the S1 level, and FIG. 4B shows a cross-section of the implant 400 at the S2 level. The implant 400 is inserted into an already distracted dorsal recess 455 in order to maintain the recess in a distracted state. The presence of the implant 400 holds the recess open after a guide tube or distractor has been utilized to maintain ligamentotaxis of the dorsal recess and/or the sacroiliac joint. In some implementations, the recess is not distracted prior to implantation, and the implant is implanted into the recess to stabilize the recess and to provide enough force to prevent the device from migration. In some implementations, the recess is not distracted prior to implantation, and the implant itself distracts the recess. In some implementations, the implant 400 serves to both distract the recess and to stabilize the recess.

As described above, the anatomy of the dorsal recess and surrounding region is variable between patients. Additionally, degenerative changes from disease, age, or defect can also alter the anatomy of the dorsal recess. For example, ilial sclerosis, subchondral cysts, or loss of cartilage can alter the shape of the dorsal recess and surrounding anatomical structures. Generally, however, the dorsal recess is formed as a double-wedge shaped recess, which is wider at the dorsal side and narrower at the ventral side, and is also wider at the rostral side and narrower at the caudal side. FIGS. 4A and 4B each shows a cross-section of the dorsal recess 455. The dorsal recess 455 is formed as a V-shape in cross-section between the sacrum 450 and ilium 452. The sacral wall 451 and the ilial wall 453 form the boundaries on either side of the dorsal recess 455. The dorsal recess 455 is typically between 25-28 mm deep (from the dorsal to ventral ends), and 2 cm wide (from the lateral to medial side), although some patients may fall outside of this range. The dorsal recess 455 can have a length between 4 mm to 50 mm, and is usually around 30 mm long, from the rostral to caudal side of the recess.

In FIG. 4A, showing the cross-section of the dorsal recess 455 at the S1 level (more caudal), the implant 400 is positioned between the sacral wall 451 and the ilial wall 453. The first planar surface 440 of the implant 400 is generally parallel to and abuts the sacral wall 451. The implant 400 is adjacent to and partially within a cut portion 456 of the ilial wall 453. The second planar surface 441 of the implant 400 is generally parallel to the ilial wall 453, though this need not be the case. The cut portion 456 of the ilial wall 453 is cut to accommodate the implant 400 when the implant 400 is positioned with the first planar surface 440 in contact with the sacral wall 451. A height 457a and 457b of the cut portion 456 extending in the ventral/dorsal direction, as well as a depth of the cut portion 456 into the ilial wall 453, is variable within the dorsal recess 455 in the rostral/caudal direction to accommodate more of the implant 400 at the narrower end of the dorsal recess at the S2 level. For example, the cut portion 456 at the S1 level has a smaller height 457a compared to the height 457b at the S2 level. The narrower dorsal recess 455 formed between the ilial wall 453 and sacral wall 451 at the S2 level in FIG. 4B benefits from a longer cut portion 457b which extends farther into the ilial wall 453 than at the S1 level shown in FIG. 4A.

The implant 400 can be any implant described herein. In some implementations, the implant 400 is constructed to approximate the shape of the dorsal recess 455. In some implementations, the implant 400 is manufactured to have the shape of the dorsal recess 455 of a particular patient, for example by 3D printing. In other implementations, the implant 400 is selected from a set of implants of varying sizes to best fit the dorsal recess 455 of the particular patient. The implant can have first and second planar side surfaces 440 and 441 which are flat so as to provide a large surface area with which to contact the sacral wall 451 (and in some cases part of the ilial wall 452) to spread the load over a larger area. In some implementations, the planar side surfaces are substantially flat or planar, though they may additionally include surface features such as spikes or ridges (not shown) for preventing movement of the implant 400. The implant can be wider at the trailing edge than at the leading edge, and as described in FIG. 3, the leading edge can be rounded to facilitate placement of the implant without being caught on anatomical features. The leading edge is positioned in the dorsal recess 455 toward the hip when the patient is on their stomach. The trailing edge is wider than the leading edge and may also be rounded or rectangular in shape.

The double-edged shape approximates the recess, but the implant 400 may still need to be accommodated by cutting or chiseling a portion of the ilial wall 453 (as will be described further below). Cutting into the ilial wall 453 to accommodate the implant 400 enables an implant of one size to be utilized in a variety of patient anatomies. The ilial wall 453 is much harder bone than the soft sacral wall, and is less likely to experience subsidence of the implant into the ilial wall 453 than the sacrum 450. Accommodating the implant 400 within a cut region 457 of the ilial wall 453 allows for a simpler surgical kit to be prepared that includes only a small number of implants 400 of different sizes or shapes. When all or a portion of the implant 400 is within the cut region 457, the second planar wall 441 of the implant 400 may or may not be parallel to the ilial wall 453. Whether all or a portion of the second planar wall 441 of the implant 400 may depend on the patient anatomy of the dorsal recess 455. An implant can be selected from the small number based on imaging or fluoroscopy of the patient dorsal recess, and the differences between the size and shape of the implant relative to the dorsal recess can be accommodated by cutting into the ilial wall 453. By cutting into the ilial wall 453, the sacral wall 451 can be preserved and is not cut during implantation. In some embodiments, the sacral wall 451 is not penetrated by the implant 400. Portions of the ilial wall 453 can be removed to accommodate implantation of the device, while no (or negligible portions) of the sacral wall 451 are cut and/or removed. In this way, the sacral wall 451 need not be cut into to accommodate the implant 400 and the implant will rest against an "uncut" (or uncompromised) surface of the sacral wall. For this reason, a small number of implant sizes (e.g., 1 to 5 implant sizes) can be utilized to treat a wide patient population. Additionally, the large planar side surfaces (first planar surface 440 and second planar surface 441) have large surface areas which contact the sacral wall 451 and the ilial wall 453, so that the implant 400 is less likely to break through the bone causing subsidence of the implant 400 into the bone. In some implementations, the sacral wall 451 is decorticated to encourage bone growth and fusion, but preferably the implant 400 is inserted without penetrating into the cortex of the sacral wall 451 so that the implant 400 lies adjacent to an outer surface of the sacrum 450.

Figures 13, 14, 15:
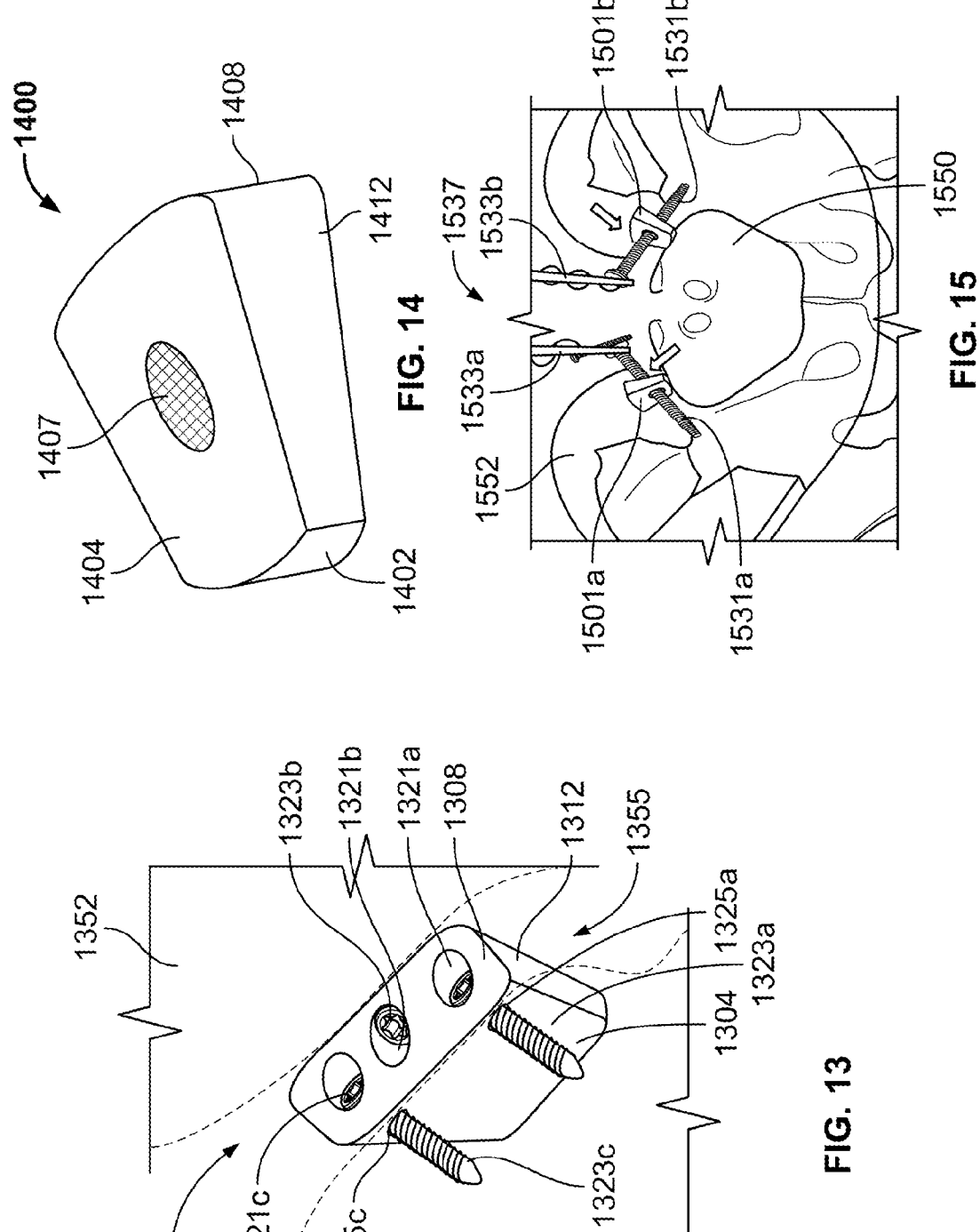
FIG. 13 shows an exemplary implant device including an internal fixation mechanism.
FIG. 14 shows an exemplary implant device including a cavity for promoting bone fusion.
FIG. 15 shows two exemplary implant devices serving as a base for a lumbo-sacral construct in a body.

Once the implant 400 is positioned in the dorsal recess 455, bone fusion between the ilium 452 and sacrum 450 can occur through cavities or windows formed in the implant 400. FIG. 14 illustrates an example of an implant 1400 having a cavity 1407 extending from the first planar surface 1404 to the second planar surface 1412, approximately parallel to the leading edge surface 1402 and trailing edge surface 1408, though this need not be the case. The implant 1400 of FIG. 14 includes the cavity 1407 for promoting bone fusion through the implant 1400. The cavity 1407 may be treated with materials or substances that promote bone growth, and in some implementations may be filled with bone material from the patient or a donor. In some implementations, the cavity 1407 can be filled with a 3-D printed tortuous structure designed to promote bone growth through the cavity. In some implementations, the implant 400 (or implant 1400 of FIG. 14) includes surface treatments to the planar side surfaces or other surfaces to encourage bone to grow onto or into the implant itself. In some implementations, the planar side surfaces or other surfaces are formed of porous materials to encourage bone in-growth into the implant. In some implementations, after the implant is positioned in the dorsal recess 455 additional bone growth material or bone material can be packed into the dorsal recess 455 with the implant for encouraging bone growth and fusion.

Figure 5:
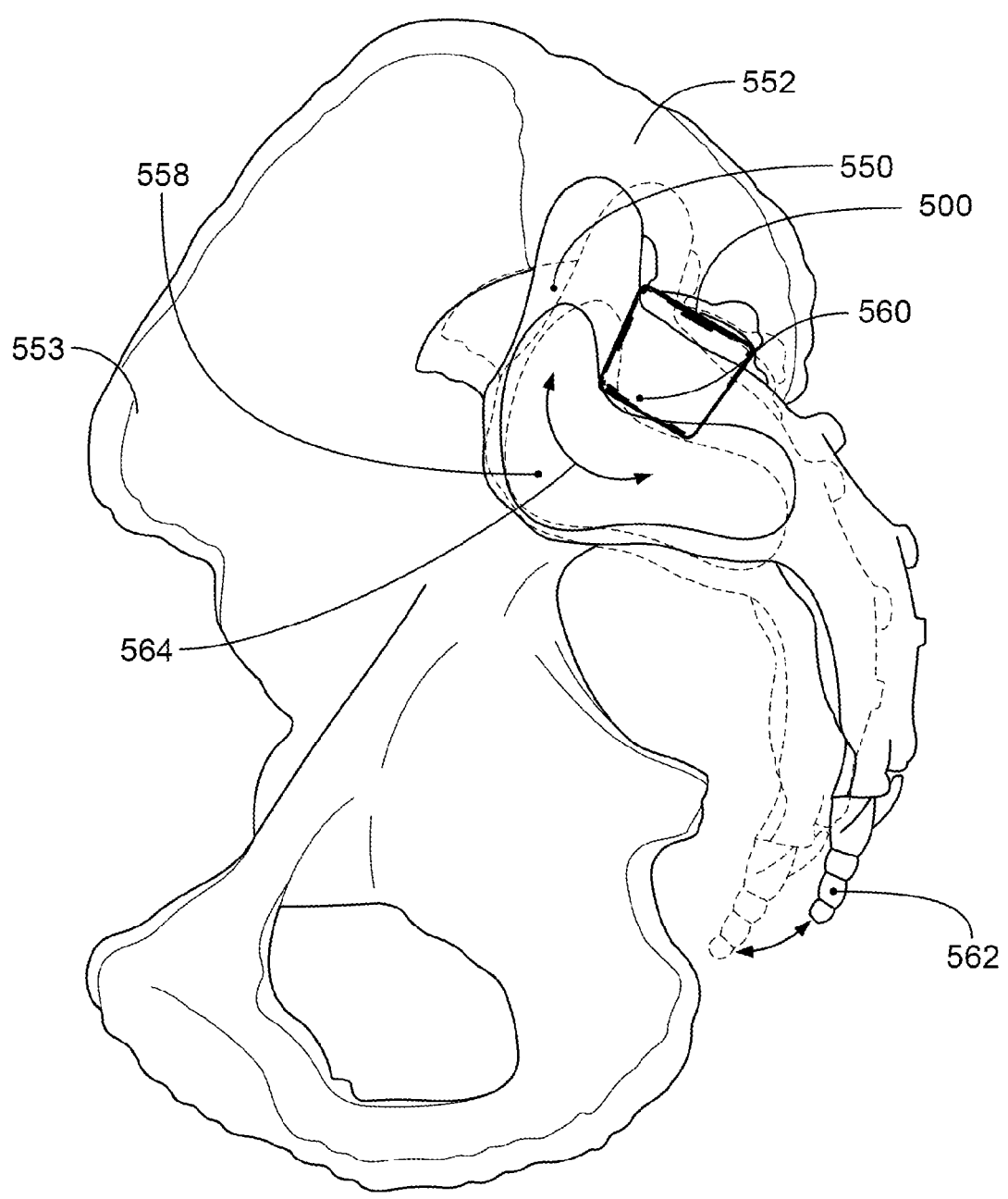
FIG. 5 shows an exemplary implant device relative to surrounding anatomy of the pelvic region.

FIGS. 5 and 6A-C illustrate the placement of the implant 500 relative to surrounding anatomy of the pelvic region. FIG. 5 shows the implant 500 in relation to the sacrum 550, sacral wall 551, ilium 552, ilial wall 553, sacroiliac joint 558 (SIJ, as defined above), and coccyx 562. The axis of nutational movement 560 is also illustrated in FIG. 5, as is the direction of nutational movement 564. The implant 500 is positioned between the sacrum 550 and ilium 552. As described above, the implant 500 is in contact with the sacral wall 551 and the ilial wall 553. The axis of nutational movement 560 describes the point about which the iliac bone 552 rotates and moves during normal motion of the patient. The direction of nutational movement 564 shows the range and direction of movement during normal motion.

Because the implant 500 is located near or at the axis of nutation movement 560, in some implementations, surface features of the implant 500 can be used to prevent migration of the implant resulting from patient motion. For example, spikes or ridges can be arranged on and perpendicular to the planar surfaces of the implant 500 to engage with the one or both of the sacral wall 551 and the ilial wall 553 to prevent movement of the implant 500. In some implementations, the spikes or ridges are arranged as concentric rings, a starburst pattern, or as etchings perpendicular to the direction of nutational movement 564 to prevent nutation, rotation, or other movement of the implant 500. Additionally, in some implementations, spikes or ridges are positioned on the planar surfaces of the implant so as to have anchors perpendicular to the pull-out direction of the implant. Additionally or alternatively, in some implementations, the implant 500 includes internal fixation mechanisms such as screws to anchor the implant 500 in place and to prevent device pullout or migration, or nutation of the sacroiliac joint.

Figure 6C:
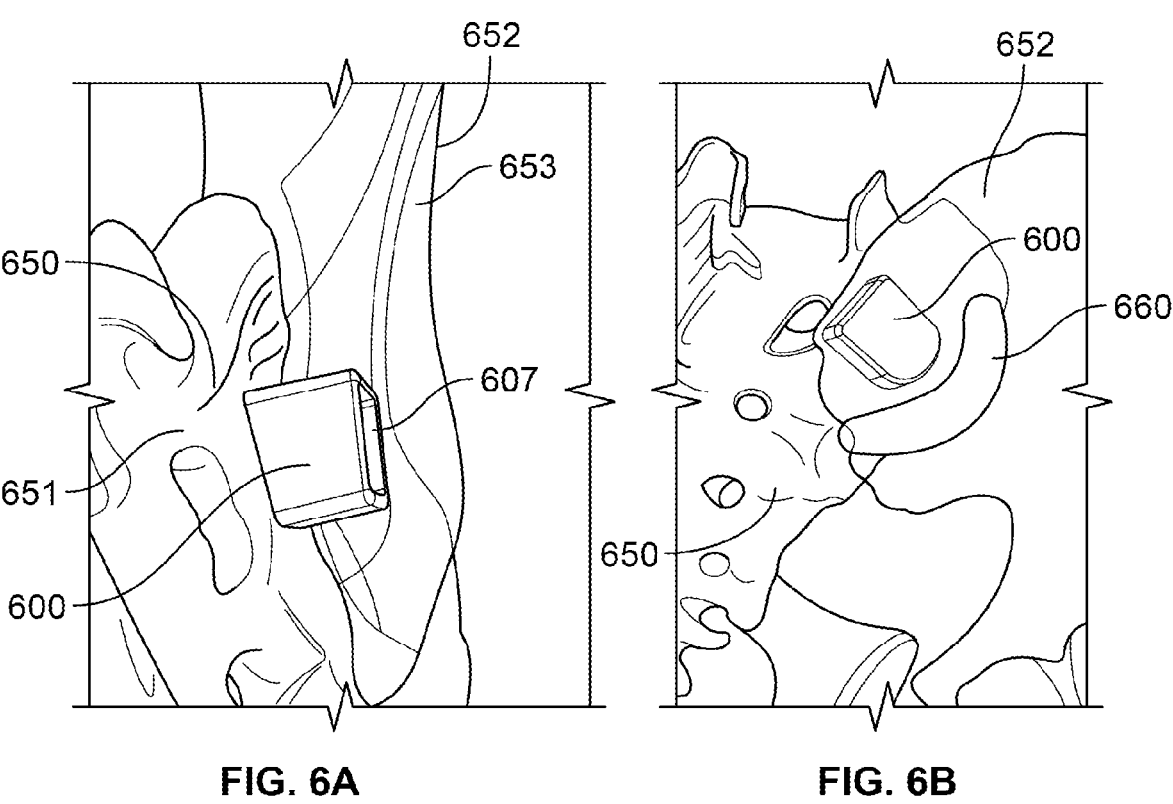
FIG. 6C shows another perspective view of an exemplary implant device positioned relative to the ilial wall.
Figure 6C:
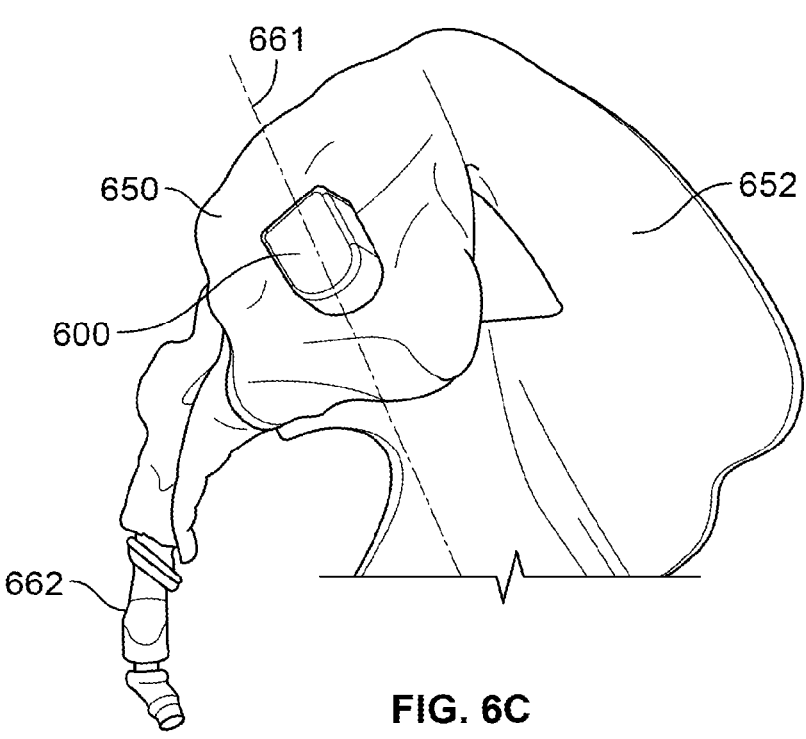

FIGS. 6A-6C show perspective views of an implant 600 positioned between the sacral wall 651 and ilial wall 653. FIGS. 6A-6C illustrate aspects of the anatomy including the sacrum 650, ilium 652, sacral wall 651, ilial wall 653, sacroiliac joint 660, and coccyx 662. The implant 600 is illustrated from different perspective views relative to the anatomical structures. In each case, the implant 600 includes planar surfaces abutting the sacral wall 651 and ilial wall 653.

FIG. 6A illustrates an implant 600 including a window 607 extending through the planar surfaces for promotion of bone growth and fusion between the sacrum 650 and ilium 652. FIG. 6B illustrates an implant 600 relative to the sacroiliac joint 660 and between the sacrum 650 and the ilium 652. FIG. 6C illustrates the implant 600 including an axis of insertion 661 along which the implant would be inserted into the dorsal recess. Insertion of the implant 600 is through a posterior approach, rather than a lateral approach. The surgeon opens an access point in the posterior of the patient, extending down to the patient's fascia, under the fascia, and along the medial side of the ilium. The posterior approach, unlike the conventional lateral approach, access is not made through muscle. The axis of insertion 661 extends toward the femoral head of the patient to orient the implant 600 with a planar surface abutting the sacral wall 651, and in some cases the ilial wall 653.

Figures 7A, 7B, 7C:
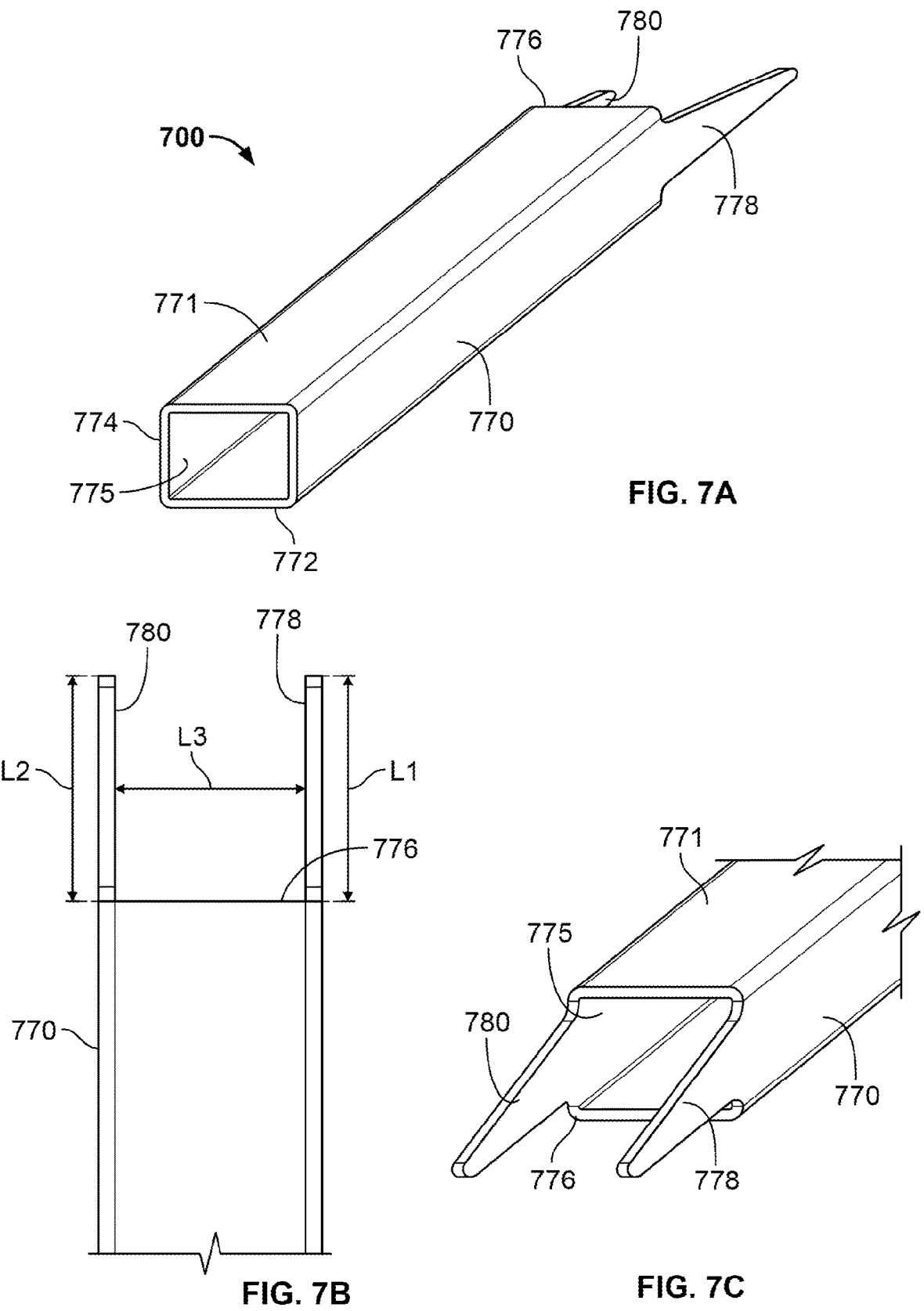
FIG. 7A shows a perspective view of an exemplary guide tube.
FIG. 7B shows a side view of an end of the guide tube of FIG. 7A.
FIG. 7C shows a perspective view of the end of the guide tube of FIG. 7B.

FIG. 7A shows a perspective view of an exemplary guide tube 700. The guide tube includes a proximal end 774, a distal end 776, an outer surface 770, first tang 778 and second tang 780. The outer surface 770 includes a first flat surface 771 and a second flat surface 772, and the outer surface 770 defines an interior channel 775 extending from the proximal end 774 to the distal end 776. The first tang 778 and the second tang 780 extend from the outer surface 770 at the distal end 776.

The first tang 778 and the second tang 780 are shaped as roughly right-angled triangular tabs extending from the distal end 776 on either side of the first flat surface 771 and second flat surface 772, such that the tangs are arranged perpendicular to the first flat surface 771 and second flat surface 772. Each of the first tang 778 and the second tang 780 have first edge which is parallel to the second flat surface 772 of the guide tube 700. In some implementations the first edge is stepped away from the second flat surface 772 so as to be parallel to the inner surface of the second flat surface 772 in the interior channel 775. The second edge of each of the first tang 778 and the second tang 780 is angled toward the first flat surface 771. The first edge of the first tang 778 and the second tang 780 is straight and parallel to the second flat surface 772 so as to be positioned parallel to the sacral wall. The angle of the second edge of the first tang 778 and the second tang 780 helps to position the guide tube 700 in the dorsal recess.

As shown in FIG. 7B, the first tang 778 extends a length L1 from the distal end 776 of the guide tube 700 outer surface 770. The second tang 780 extends a length L2 from the distal end 776. The first tang 778 and the second tang 780 are spaced apart by length L3. L3 is measured parallel to the first flat surface 771 and second flat surface 772. In some implementations, L1 and L2 are the same length. In some implementations, L1 is greater than L2. In some implementations, L1 is less than L2.

FIG. 7C shows a perspective view of the distal end 776 of guide tube 700. The first tang 778 and second tang 780 are extensions of the outer surface 770 of the guide tube between the first flat surface 771 and second flat surface 772. The first tang 778 and second tang 780 are shown as triangular tabs having a rounded tip. In some implementations, the first tang 778 and second tang 780 are symmetrical, that is they are the same in shape and size. In some implementations, the first tang 778 and second tang 780 are asymmetrical and are different in at least one dimension or aspect. For example, the first tang 778 and second tang 780 can be different shapes and sizes to preferentially orient the guide tube 700 within the dorsal recess. The first tang 778 can be narrower, thinner, or more steeply angled than the second tang 780, so as to position the guide tube 700 within the dorsal recess at the S2 level, where the recess may be narrower. The second tang 780 can aid in positioning the guide tube 700 at the S1 level, as will be further described below.

Figure 8:
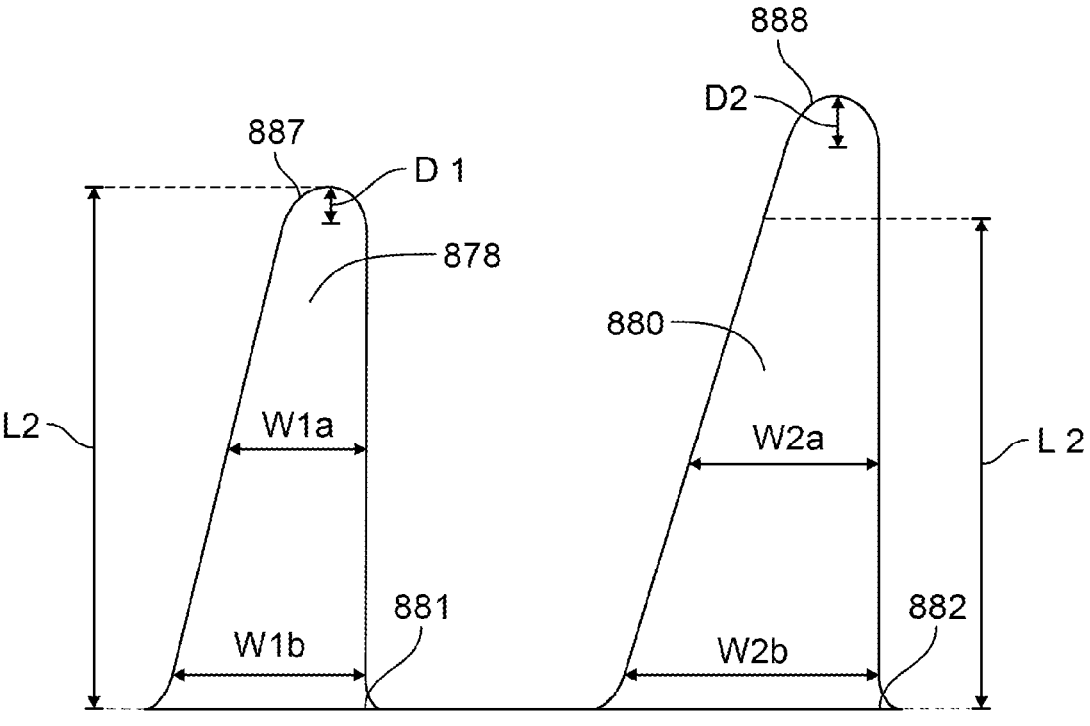
FIG. 8 shows a side view of exemplary tangs of the guide tube of FIG. 7A.

FIG. 8 shows a side view of exemplary tangs of the guide tube of FIG. 7A. The first tang 878 has a length L1 extending from the base 881 of the first tang 878 to the tip 887. The first tang 878 has a width at the bottom of W1$b$ and a width at a mid-point of the length L1 of W1$a$. The tip 887 is rounded and has a radius of curvature of D1. The second tang 880 has a length L2 extending from the base 882 of the second tang 880 to the tip 888. The second tang 880 has a width at the bottom of W2$b$ and a width at a mid-point of the length L2 of W2$a$. The tip 888 is rounded and has a radius of curvature of D2.

In FIG. 8, first tang 878 is taller and narrower in shape than the second tang 780. In particular, the first tang 878 has a greater length L1 than the length L2 of the second tang 880. Additionally, W1$b$ and W1$a$ are less than W2$b$ and W2$a$, respectively. Finally, D1 is less than D2. The narrower first tang 878 is able to fit into the dorsal recess at the narrower S2 level, while the wider second tang 880 fits into the dorsal recess at the S1 level. The first tang 878 and second tang 880 can be inserted into the recess to orient the guide tube, because the tangs will fit only in a certain portion of the dorsal recess (the S1 and S2 levels) and can only be inserted to a point before force is necessary. Though the first tang 878 and second tang 880 are each illustrated as a substantially triangular tab which is symmetrical about a central axis, the first tang 878 and second tang 880 need not be symmetrical about the central axis. In some implementations, a leading edge of each of the first tang 878 and second tang 880 is angled, and a trailing edge is substantially straight. The geometry of the first tang 878 and second tang 880 can aid in positioning the guide tube in the anatomy to ensure proper positioning of the implant with a planar wall parallel to the sacrum.

Figure 9:
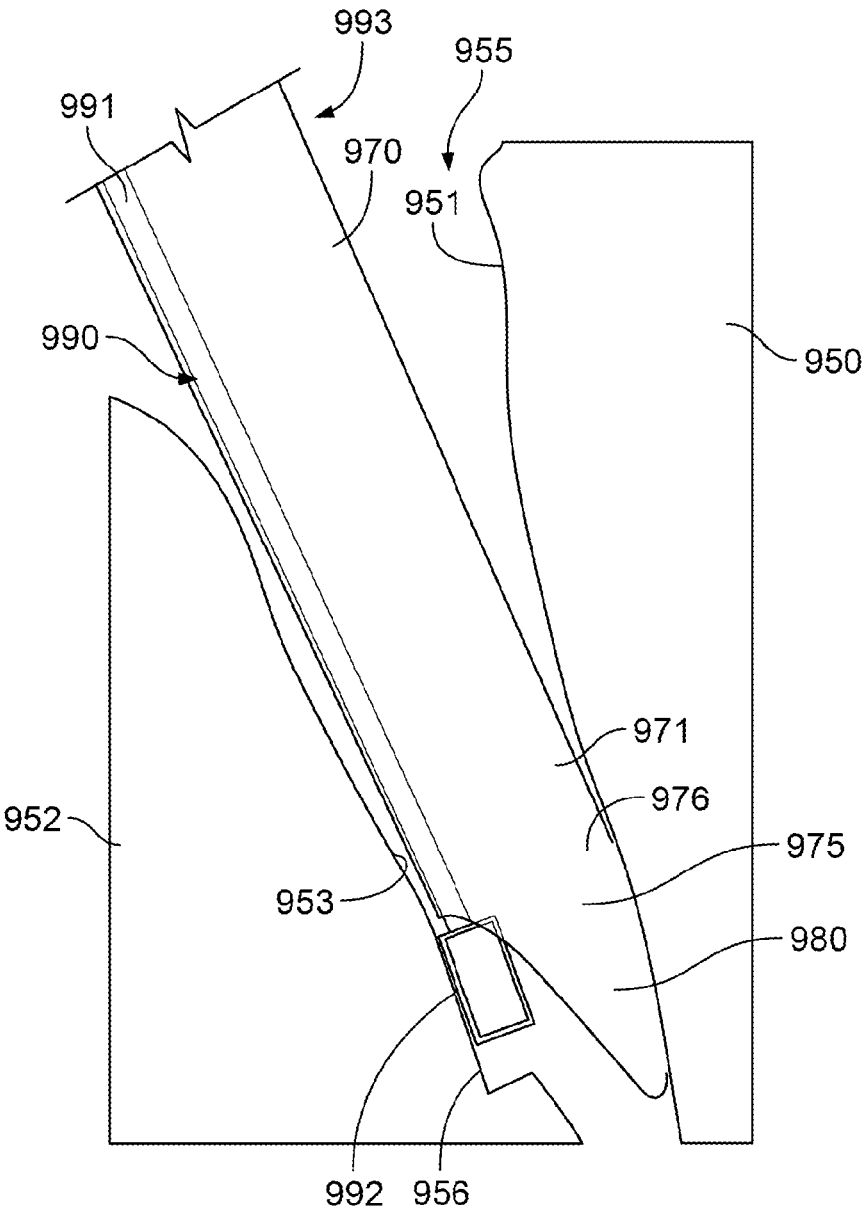
FIG. 9 shows a perspective view of a guide tube and cutting device positioned in a recess.

FIG. 9 shows a perspective view of a guide tube 970 and cutting device 990 positioned in a recess 955. The guide tube 993 (for example, guide tube 700 of FIGS. 7A-C) includes an outer surface 970, a first flat surface 971, an interior channel 975, a distal end 976, and a second tang 980 (note that FIG. 9 shows the guide tube 993 in profile, and first tang is hidden from view behind second tang 980). The cutting device 990 includes an elongate handle 991 and cutting surface 992 at a distal end of the elongate handle 991.

As described above, the guide tube 993 is positioned in the recess 955 formed between the sacrum 950 and ilium 952 by inserting the guide tube 993 with the first tang (not shown) and second tang 980 oriented with the first tang at the S2 level and the second tang 980 at the S1 level in the recess. The shape of the first tang and the second tang 980 orients the guide tube 993 such that a flat surface 971 of the guide tube 993 is parallel to the sacral wall 951. The interior channel 975 is also parallel to the sacral wall 951 when the flat surface 971 of the guide tube 993. Because the sacral wall 951 can have various shapes and features, the flat surface 971 of the guide tube 993 can be substantially parallel to the sacral wall 951, or parallel to a portion of the sacral wall 951 within the dorsal recess, and need not be entirely parallel to the sacral wall 951 in its entirety.

After the guide tube 993 is positioned in the recess 955, the cutting device 990 is inserted through the interior channel 975 of the guide tube 993. The cutting surface 992 is coupled to the distal end of the elongate handle 991 to enable manipulation of the cutting surface 992 when the cutting device 990 is positioned in the dorsal recess 955 through the guide tube 993. The cutting device 990 extends from the interior channel 975 of the guide tube at the distal end 976 between the first tang and the second tang 980.

The cutting device 990, extending through the guide tube 993 parallel to the sacral wall 951, is also parallel to the sacral wall 951. The cutting device 990 can be manipulated to penetrate a portion of the ilial wall 953 and to cut a portion of the ilium 952 to remove bone. The portion of bone (the "cut portion" 956 of the ilium 952) to be removed from the ilial wall 953 by the cutting device 990 is determined by the surgeon based on imaging methods, fluoroscopy, or visual cues regarding the shape and size of the patient's dorsal recess 955 compared to the size and shape of the implant to be positioned in the dorsal recess 955. Removal of the portion of the ilial wall 953 with the cutting device 990 forms a cut portion 956, or a cavity, within the ilium 952. The tissue and bone of the ilial wall 953 are cut away to accommodate the size and shape of the intended implant based on the distance from the sacral wall 951, to which the guide tube 993 is adjacent and parallel. As described above with regard to FIG. 4, the amount of bone removed from the ilial wall 953 may vary along the length of the recess 955, as the recess 955 narrows toward the S2 level, and more material may need to be removed to accommodate the implant. The sacral wall 951 is not penetrated (e.g., portions of the wall are not removed or "violated") during the cutting of the cavity, though in some cases the sacral wall 951 can be decorticated to encourage bone fusion.

The cutting surface 992 is depicted as a box-shaped cutter, for cutting ilial wall 953. In some implementations, the cutting surface 992 is an L-shaped cutter without a surface for cutting facing the sacral wall 951 to prevent any damage to the sacral wall 951. In some implementations, the cutting surface 992 is a rasp, a chisel, a curette, a scalpel, a blade, or any other suitably shaped and sized cutter. In some implementations, the cutting device 990 is a reamer.

In some implementations, additional tools can be inserted and manipulated through the guide tube 993. For example, lights can be inserted into the guide tube 993 to illuminate the recess for better visualization during the removal of ilial bone. A chisel may be inserted through the guide tube in addition or alternatively to the cutting surface 992 for removal of the portion of the ilial wall 953.

After removal of a portion of bone from the ilial wall 953 (forming the cut portion 956), the cutting device 990 can be removed, and the implant 900 can be inserted. The insertion of the guide tube 993 into the dorsal recess holds open the distracted dorsal recess until the implant is in position. In some implementations, a distractor is utilized prior to insertion of the guide tube 993 to open the dorsal recess, and the guide tube 993 is inserted to maintain ligamentotaxis of the dorsal recess and/or the sacroiliac joint.

Figure 10:
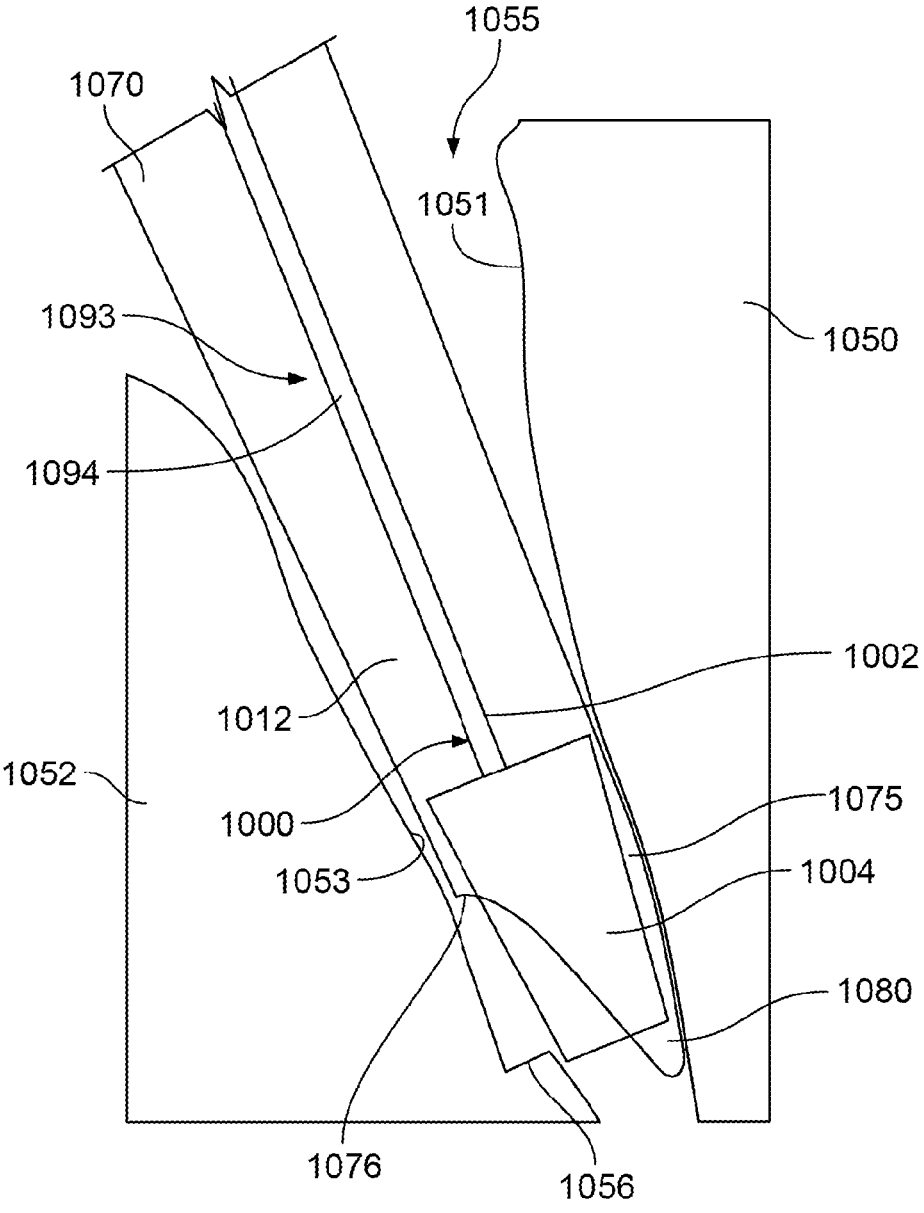
FIG. 10 shows a perspective view of a guide tube and implant device positioned in a recess.

FIG. 10 shows a perspective view of a guide tube 1093 and implant device 1000 positioned in a recess 1055 prior to implantations. The guide tube 1093 (for example, guide tube 700 of FIGS. 7A-C, guide tube 993 of FIG. 9, or guide tube 1093 of FIG. 10) includes an outer surface 1070, an interior channel 1075, a distal end 1076, and a second tang 1080 (note that FIG. 10 shows the guide tube 1093 in profile, and first tang is hidden from view behind second tang 1080). The implant 1000 (such as implant 100 of FIGS. 1A-G, implant

200 of FIGS. 2A-C, implant 300 of FIG. 3, implant 400 of FIGS. 4A-B, implant 500 of FIG. 5, implant 600 of FIGS. 6A-C) includes a leading edge surface 1002, a first planar side surface 1004 and a second planar side surface 1012. The implant 1000 is coupled to an inserting device 1094.

The implant 1000 is inserted through the guide tube 1093. Because the guide tube 1093 (or a flat surface formed on the outer surface 1070) is parallel to the sacral wall 1051, the implant 1000 is inserted through the interior channel 1075 of the guide tube 1093 so as to be parallel to the sacral wall 1051. In some implementations, the first planar surface 1004 of the implant 1000 is inserted into the guide tube 1093 facing a flat exterior and/or interior of the guide tube 1093, and is guided to be parallel to and abutting the sacral wall 1051 by the guide tube 1093.

The implant 1000 is aligned with the sacral wall 1051 by the guide tube 1093, and is inserted into the dorsal recess 1055 between the sacrum 1050 and the ilium 1052. The implant 1000 extends between the first tang (not shown) and the second tang 1080, and into the cut portion 1056 of the ilial wall 1053. In some implementations, the implant 1000 may be further manipulated, for example by use of a hammer, to be positioned in the dorsal recess 1055 to provide distraction and fusion.

Once the implant 1000 is in place between the sacrum 1050 and ilium 1052, the implant 1000 can be released from the inserting device 1094, and the inserting device 1094 can be removed from the dorsal recess 1055 through the guide tube 1093. The implant 1000 is coupled to the inserting device 1094 by a screw mechanism, a prong-based mechanism, or another suitable mechanism. The inserting device 1094 may be formed as an elongate shaft with a proximal handle (not shown). The handle may include mechanisms for release of the implant 1000 after the implant 1000 has been positioned in the dorsal recess 1055, or the handle can be turned to unscrew the elongate shaft of the inserting device 1094 from the implant 1000. In such cases, the implant 1000 includes at least one bore hole, indentation, or other engagement mechanism for coupling with the inserting device 1094.

By removing tissue from the ilial wall 1053 to accommodate the implant 1000, the cortex of the sacral wall 1051 is preserved, and risk of subsidence of the implant 1000 into the soft sacrum 1050 is reduced. The implant 1000 can maintain the distraction (and/or in some cases stabilization) of the dorsal recess 1055 with large planar surfaces in contact with the ilial wall 1053 and sacral wall 1051. The large planar surfaces, which have large surface area in comparison to conventional devices, further minimize risk of subsidence of the implant 1000 into the sacral bone and failure of the implant.

Figure 11:
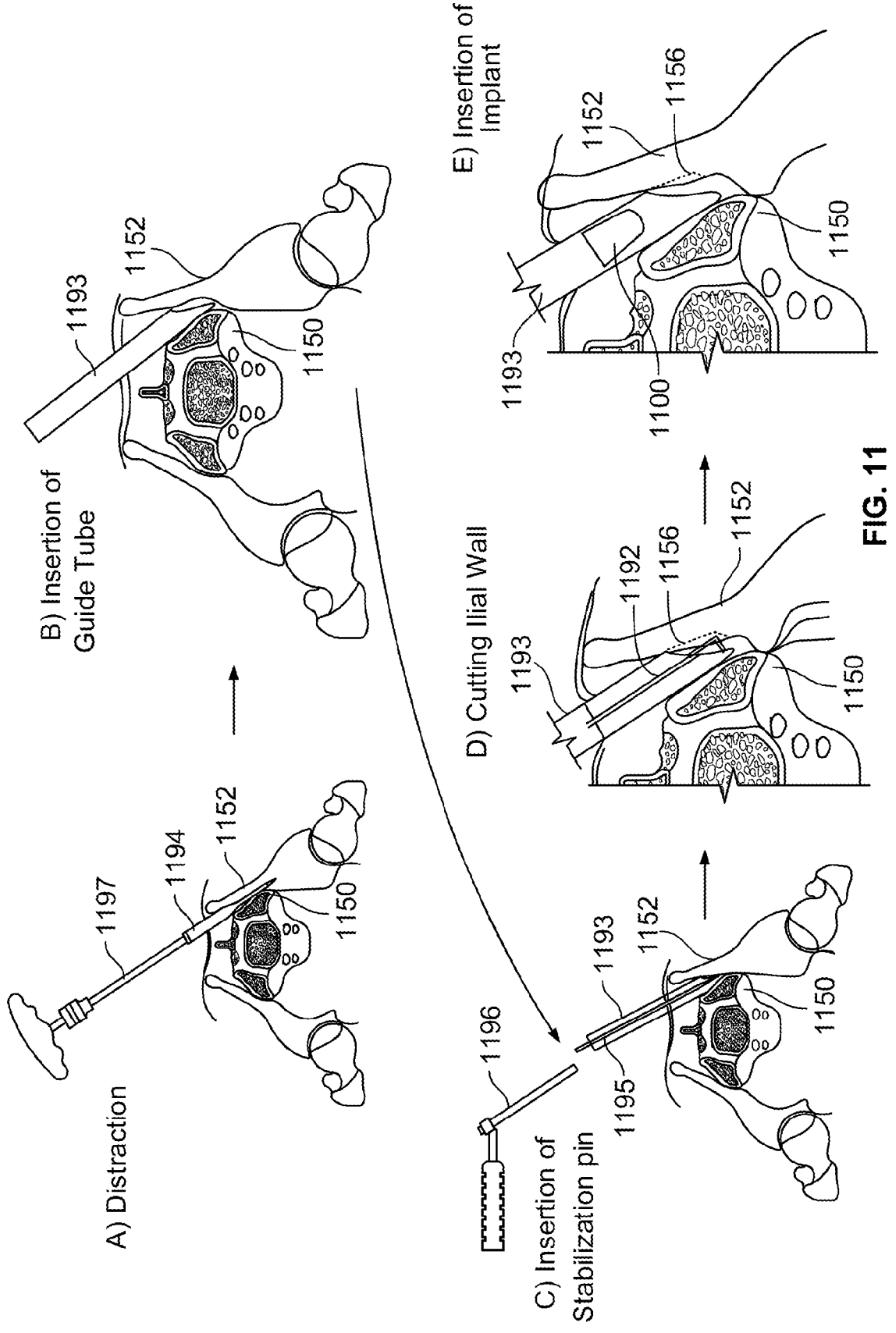
FIG. 11 shows a flow diagram of steps of a surgical method for implanting an implant device in a recess.
Figure 12:
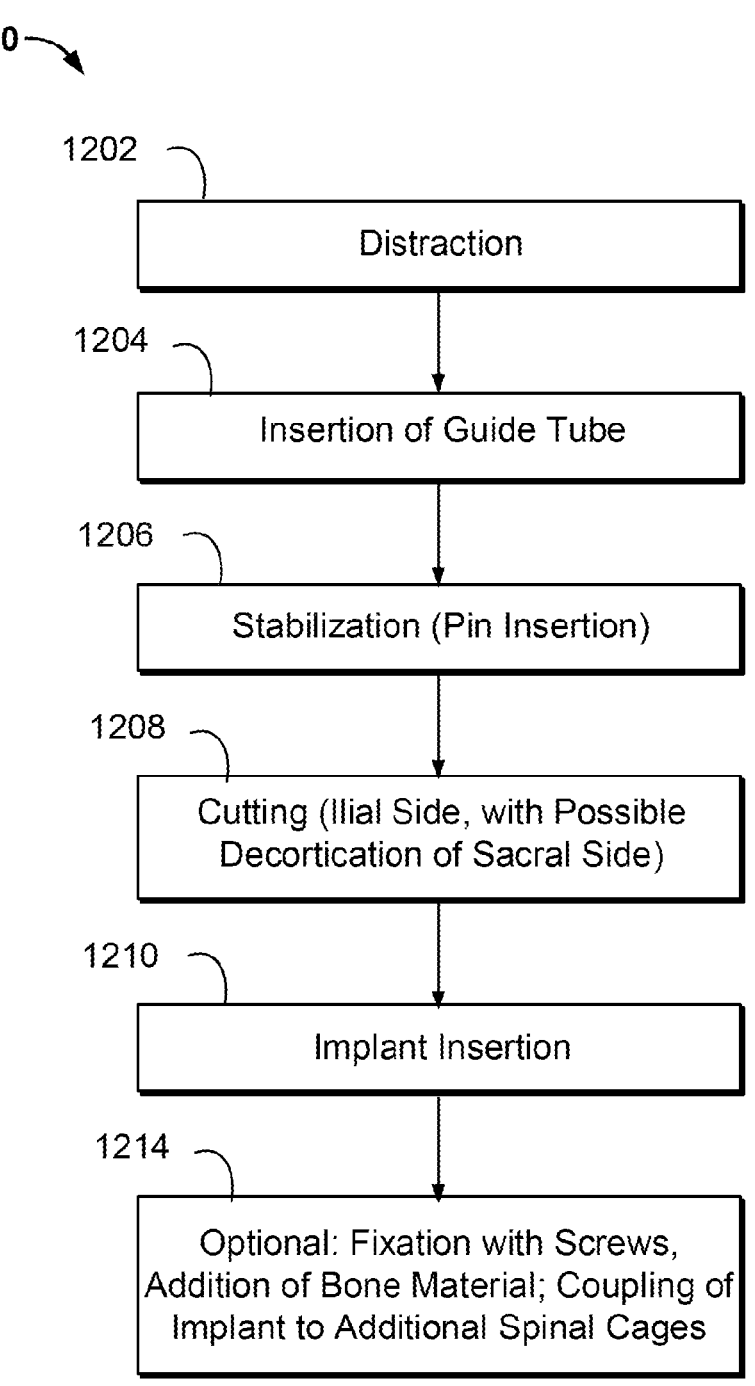
FIG. 12 shows a flow chart of a surgical method for implanting an implant device in a recess.

FIG. 12 shows a flow chart of a surgical method 1200 for implanting an implant device in a recess. The method is illustrated in FIG. 11 as flow diagram of steps of a surgical method for implanting an implant device in a recess, and FIG. 11 will be referred to in the context of the method of FIG. 12. As illustrated in FIG. 11 at (A), the method begins at step 1202 by distracting the recess between the ilium 1152 and the sacrum 1150 using a distractor 1194 or other tool. The distractor 1194 can include an elongate handle 1197 for manipulating the distractor. The distractor 1194 opens the recess between the sacrum 1150 and the ilium 1152. In some implementations, the distraction is accomplished by insertion of the guide tube into the recess. As illustrated in FIG. 11 at (B), at step 1204, the method includes inserting the guide tube 1193 into the recess between the ilium 1152 and the sacrum 1150 to guide the implantation trajectory and orientation of the implant device. The guide tube 1193 can be oriented in the recess using visual cues and guides visible to the surgeon, using imaging techniques or fluoroscopy, or by features of the guide tube 1193 itself which position the guide tube 1193 in the recess. For example, the guide tube illustrated in FIGS. 7-9 includes asymmetric tangs (described above) which orient a flat or planar surface of the guide tube to be parallel to the sacral wall by fitting into the dorsal recess at the 51 and S2 levels.

At step 1206, illustrated in FIG. 11 at (C), the guide tube 1193 is stabilized in place by the insertion of a pin 1195. The pin 1195 can be inserted using a pin inserter device 1195 which can include a handle and an elongate guide 1196 for placing the pin 1195. In some implementations, the guide tube 1193 includes one or more guides or channels through which the pin 1195 can be inserted to anchor the guide tube 1193 in position parallel to at least a portion of the wall of the sacrum 1150. In some implementations, the pin 1195 is inserted into the ilium 1152. In some implementations, one or both tangs of the guide tube 1193 include an opening through which the stabilization pin 1195 can be inserted. As illustrated in FIG. 11 at (D), at step 1208, a cutting device 1192, such as a box-cutter, L-shaped cutter, reamer, or other cutting device, is inserted through the guide tube 1193 and positioned adjacent the wall of the ilium 1152. The cutting device 1192 is then used to remove a portion of the wall of the ilium 1152. The cutting device 1192 is preferably shaped to cut into the wall of the ilium 1152 to form a cut portion 1156 in a shape to accommodate the implant, without cutting the wall of the sacrum 1150. In some implementations, the sacral wall 1150 is decorticated to encourage bone growth and fusion, but preferably the implant is inserted without penetrating into the cortex of the sacral wall 1150 so that the implant lies adjacent to an un-cut surface of the sacrum 1150.

At step 1210, illustrated in FIG. 11 at (E), the implant 1100 is inserted through the guide tube 1193 into the distracted recess between the ilium 1152 and the sacrum 1150. The implant 1100 is positioned so that one planar surface is parallel to and in contact with an uncut surface of the sacrum 1150 and the opposite planar surface of the implant 1100 is in contact with the cut portion 1156 of the sacrum 1152. The implant 1100 can be inserted using any suitable inserter. The inserter may include an elongate handle which is coupled to the implant by a screw device or prongs (not shown). The implant 1100 is positioned in the recess so as to maintain the distraction of the ilium 1152 and the sacrum 1150 to provide relief and treatment to the patient.

Optionally, at step 1212, various additional steps may be taken that are not required or necessary but may be beneficial or advantageous in certain instances. For example, screws may be utilized to fix the implant in place in the recess in order to prevent back-out or migration of the implant. As another example, bone material can be added to a cavity of the implant or to the recess following insertion of the implant to encourage bone growth and fusion. In another example, the implant can serve as a base for additional spinal implants and devices, and the implant can be coupled to and for a base for a spinal cage or lumbo-sacral construct.

Depending on the use of the implant, the implant can be manufactured and made available as part of a kit including the surgical components for placement of the implant. The kit includes multiple sizes and/or geometries of implants (for example, small, medium, and large or slightly angled, more angled, not angled). Because the ilial wall is cut into to accommodate the implant, a perfect fit to the patient anatomy is not required, and fewer implants can be included in a kit. The kit also includes a guide tube for positioning the implant in the dorsal recess. The kit may also include one or more of a rectangular-shaped cutting device, an L-shaped cutting device, a box-cutter, a box chisel, a curette, a distractor, a rasp, an inserting device, a removing device, one or more screws, a hammer, and a pin.

FIG. 13 shows an exemplary implant 1300 including an internal fixation mechanism. The implant 1300 includes a first planar surface 1304, a second planar surface 1312, and trailing edge surface 1308. Trailing edge surface 1308 includes screw openings 1321*a*, 1321*b*, and 1321*c*, and first planar surface 1304 includes screw exits 1325*a* and 1325*c*. A screw exit formed in the second planar surface 1312 is not shown. Screws 1323*a*, 1323*b*, and 1323*c* extend through the screw openings 1321*a*, 1321*b*, and 1321*c* to screw exits 1325*a*, 1325*c* (1325*b* not shown). The implant 1300 is positioned in the dorsal recess 1355 between the sacrum 1350 and the ilium 1352.

The screws 1323*a*, 1323*b*, and 1323*c* act as internal fixation mechanisms that attach the implant 1300 to the surrounding anatomy to prevent motion or migration of the implant 1300. The screws 1323*a*, 1323*b*, and 1323*c* can be inserted into one or both of the ilium 1352 and sacrum 1350 to fix the implant 1300 in position. In some implementations, screws are only inserted into the ilium 1352. In other implementations, screws are inserted into both the ilium 1352 and the sacrum 1350.

FIG. 15 shows two exemplary first and second implant devices 1501*a* and 1501*b* positioned between the sacrum 1550 and the ilium 1552 serving as a base for a lumbo-sacral construct 1537 in a body. The lumbo-sacral construct 1537 includes a first cage portion 1533*a* and a second cage portion 1533*b* extending up the spinal column. A first bolt 1531*a* extends from a bottom portion of the first cage portion 1533*a* through the first implant 1501*a*. The first bolt 1531 can extend into the ilium 1552. A second bolt 1531*b* extends from a bottom portion of the second cage portion 1533*b* through the first implant 1501*b*, and into the ilium 1552.

Using SIJ implants as a base for a lumbo-sacral construct or other spinal cage or device can help to stabilize the construct. By coupling the construct to the implants 1501*a* and 1501*b*, the lumbo-sacral construct is stabilized using both screws and implants that will be fused in the dorsal recess.

FIG. 16 shows a flow chart of a method 1600 for stabilizing and fusing a sacroiliac joint. At step 1602, the dorsal recess is distracted. The dorsal recess is formed by a sacral wall and an ilial wall (as illustrated in FIGS. 4A and 4B). The distraction of the dorsal recess widens the recess and can take remove some stress from the region. In some implementations, the dorsal recess is not distracted prior to implantation of the implant to stabilize the sacroiliac joint or surrounding region.

Optionally, at step 1604, a guide tube (for example, guide tube 700 of FIGS. 7A-C, guide tube 993 of FIG. 9, or guide tube 1093 of FIG. 10) is inserted into the dorsal recess between the sacral wall and the ilial wall (as illustrated in FIGS. 9 and 10). The guide tube is positioned so as to be parallel to at least a portion of the sacral wall. Optionally, at step 1606, a stabilization pin is inserted to secure the position of the guide tube is secured within the dorsal recess and parallel to a portion of the sacral wall.

At step 1608, a surface of the ilial wall is cut using a cutting device (such as cutting device 990 of FIG. 9). In some implementations, the cutting device is inserted through the guide tube and used to cut a surface of the ilial wall, forming a cavity shaped and sized to accommodate a portion of the implant. The cut surface of the ilial wall is cut relative to the sacral wall.

At step 1610, the implant (such as implant 100 of FIGS. 1A-G, implant 200 of FIGS. 2A-C, implant 300 of FIG. 3, implant 400 of FIGS. 4A-B, implant 500 of FIG. 5, implant 600 of FIGS. 6A-C, implant 1000 of FIG. 10, implant 1300 of FIG. 13, implant 1400 of FIG. 14, or implant 1500 of FIG. 15) is positioned in the distracted recess such that at least a portion of the implant is in contact with the cut surface of the ilial wall. The implant includes a first planar wall and a second planar wall opposite the first planar wall, and is positioned in the recess so that the first planar wall of the implant is in contact with an uncut surface of the sacral wall. Accordingly, the method of implantation includes cutting and/or removing a portion of the ilial wall to accommodate the implant, instead of removing portions of the sacral cortex. This can eliminate the need to remove any material or at least reduce the amount of material removed from the sacral bone during implantation. The implant serves to maintain the distraction of the dorsal recess, and can also facilitate bone growth and fusion of the sacrum and ilium.

While this specification contains many specific implementation details, these should not be construed as limitations on the scope of the disclosed technology or of what may be claimed, but rather as descriptions of features that may be specific to particular implementations of particular disclosed technologies. Certain features that are described in this specification in the context of separate implementations can also be implemented in combination in a single embodiment in part or in whole. Conversely, various features that are described in the context of a single embodiment can also be implemented in multiple implementations separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in a sequential order, or that all operations be performed, to achieve desirable results. Particular embodiments of the subject matter have been described. Other embodiments are within the scope of the following claims.

We claim:

1. A method of treating a sacroiliac joint and/or a region proximate the sacroiliac joint, the method comprising:
 distracting a recess between a sacral wall of a sacrum and an ilial wall of an ilium;
 cutting a surface of the ilial wall using a cutting device, wherein the sacral wall is not penetrated by the cutting device; and
 positioning an implant having a first planar wall and a second planar wall opposite the first planar wall into the distracted recess, such that the first planar wall of the implant is in contact with an uncut surface of the sacral wall, and the second planar wall is in contact with the cut surface of the ilial wall.

2. The method of claim 1, wherein each of the first and second planar walls are defined by at least one first side edge and a second side edge, the first side edge of the first planar wall is distanced from the first side edge of the second planar wall by a first separation distance, and the second side edge of the first planar wall is distanced from the second side edge of the second planar wall by a second separation distance; and wherein the first separation distance is smaller than the second separation distance.

3. The method of claim 2, wherein the implant comprises:
 third and fourth planar walls each extending between the first and second planar walls, the third planar wall extending between a third side edge of the first planar wall and a third side edge of the second planar wall, the fourth planar wall extending between a fourth side edge of the first planar wall and a fourth side edge of the second planar wall,
 wherein the third planar wall has a length that is shorter than that of the fourth planar wall.

4. The method of claim 1, further comprising:
 inserting a guide tube into the recess between the sacral wall and the ilial wall;
 positioning the guide tube within the recess using two distal tangs of the guide tube, the two distal tangs being asymmetrically formed to fit within the recess;
 anchoring, using a pin, the guide tube within the recess and parallel to at least a portion of the sacral wall; and
 inserting the implant into the recess through the guide tube.

5. The method of claim 4, further comprising: creating a surgical access point for inserting the guide tube into the recess by a posterior approach.

6. The method of claim 4, wherein the implant is shaped as of one of a cuboid, a rectangular cuboid, a wedge-shaped cuboid, and a double-wedge-shaped cuboid.

7. The method of claim 6, wherein at least one surface of the implant is a curved surface.

8. The method of claim 4, wherein cutting the surface of the ilial wall using the cutting device further comprises: inserting the cutting device through the guide tube; penetrating, with the cutting device, a portion of the ilium; and removing, with the cutting device, a portion of the ilial wall to form a cavity within the ilium.

9. The method of claim 8, further comprising: inserting a screw through a hole of the implant into the ilial wall, the screw configured to serve as a base of a lumbo-sacral construct.

10. The method of claim 8, further comprising: inserting at least one screw through a screw hole of the implant into at least one of the ilial wall and the sacral wall.

\* \* \* \* \*